United States Patent
Kawaura et al.

(10) Patent No.: US 9,713,517 B2
(45) Date of Patent: Jul. 25, 2017

(54) METHOD OF PLACING IMPLANT INDWELLING

(71) Applicant: TERUMO KABUSHIKI KAISHA, Shibuya-ku (JP)

(72) Inventors: Masakatsu Kawaura, Sunnyvale, CA (US); Nao Yokoi, Sunnyvale, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 263 days.

(21) Appl. No.: 14/489,958

(22) Filed: Sep. 18, 2014

(65) Prior Publication Data
US 2015/0087895 A1    Mar. 26, 2015

(30) Foreign Application Priority Data
Sep. 20, 2013   (JP) ................. 2013-196172

(51) Int. Cl.
*A61F 2/00*   (2006.01)
*A61B 17/34*  (2006.01)

(52) U.S. Cl.
CPC ........ *A61F 2/0045* (2013.01); *A61B 17/3403* (2013.01); *A61B 17/3468* (2013.01); *A61F 2/0063* (2013.01); *A61F 2002/0072* (2013.01); *A61F 2220/0016* (2013.01); *A61F 2230/0019* (2013.01)

(58) Field of Classification Search
CPC .................. A61F 2/0045; A61F 2/0063; A61F 2002/0072; A61F 2220/0016; A61F 2230/0019; A61B 17/3403; A61B 17/3468
See application file for complete search history.

(56) References Cited

U.S. PATENT DOCUMENTS

| | | | |
|---|---|---|---|
| 6,911,003 B2 | 6/2005 | Anderson et al. | |
| 7,527,588 B2* | 5/2009 | Zaddem | A61B 17/0482 600/29 |
| 2002/0055748 A1* | 5/2002 | Gellman | A61B 17/00234 606/139 |
| 2003/0062052 A1* | 4/2003 | Carter | A61B 17/062 128/885 |
| 2004/0225181 A1* | 11/2004 | Chu | A61B 17/06109 600/37 |
| 2011/0152914 A1* | 6/2011 | Ostrovsky | A61F 2/0045 606/193 |

FOREIGN PATENT DOCUMENTS

| | | |
|---|---|---|
| JP | 2010-099499 A | 5/2010 |
| WO | WO 03/075792 A1 | 9/2003 |

* cited by examiner

*Primary Examiner* — Christine H Matthews
*Assistant Examiner* — Kaylee Wilson
(74) *Attorney, Agent, or Firm* — Buchanan Ingersoll & Rooney PC

(57) ABSTRACT

A method of placing an implant indwelling in a living body is disclosed. The method can include forming an insertion hole in the living body, the insertion hole extending from a living body surface and passing an obturator foramen on one side and an obturator foramen on the other side, the insertion hole having its end portion on the one side opened in the living body surface and its end portion on the other side closed in relation to the living body surface; inserting a medical tube that permits the implant to be inserted into the medical tube, prior to insertion of the implant; inserting the implant into the medical tube inserted in the insertion hole; and pulling the medical tube out of the insertion hole so that the implant is placed indwelling in the living body.

14 Claims, 23 Drawing Sheets

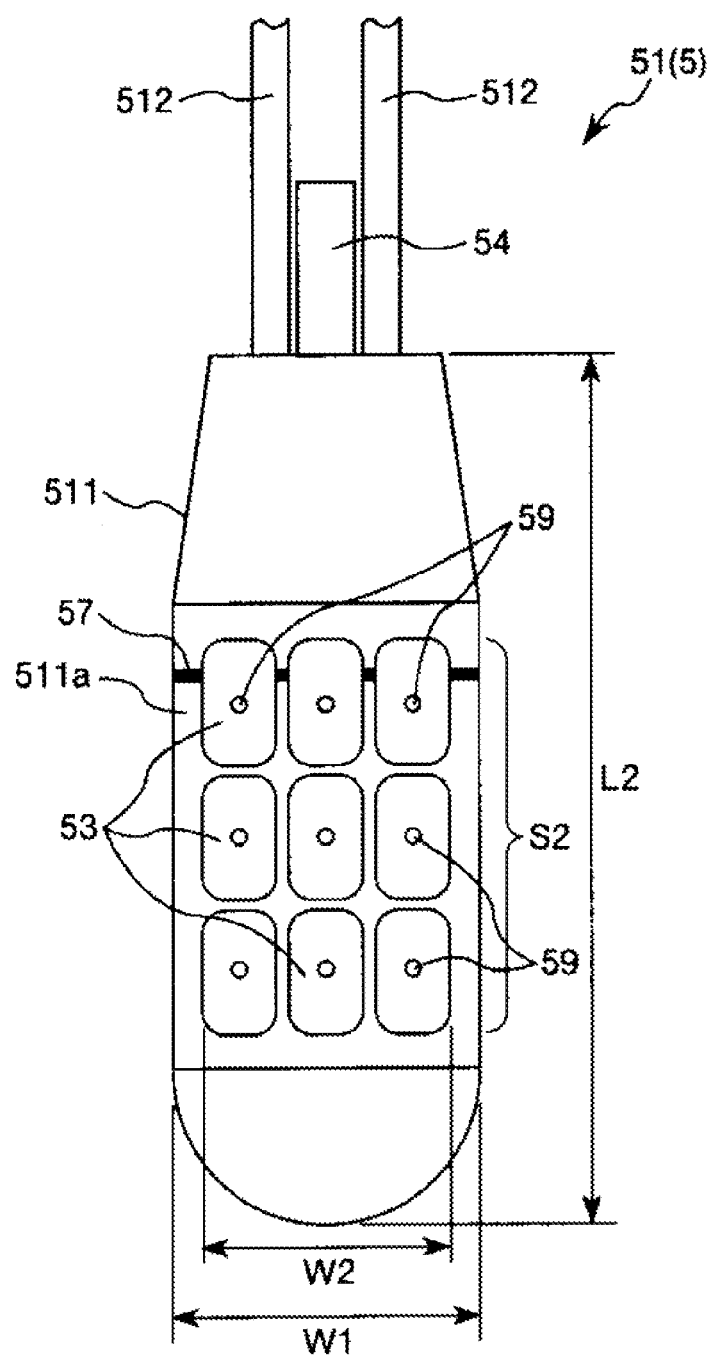

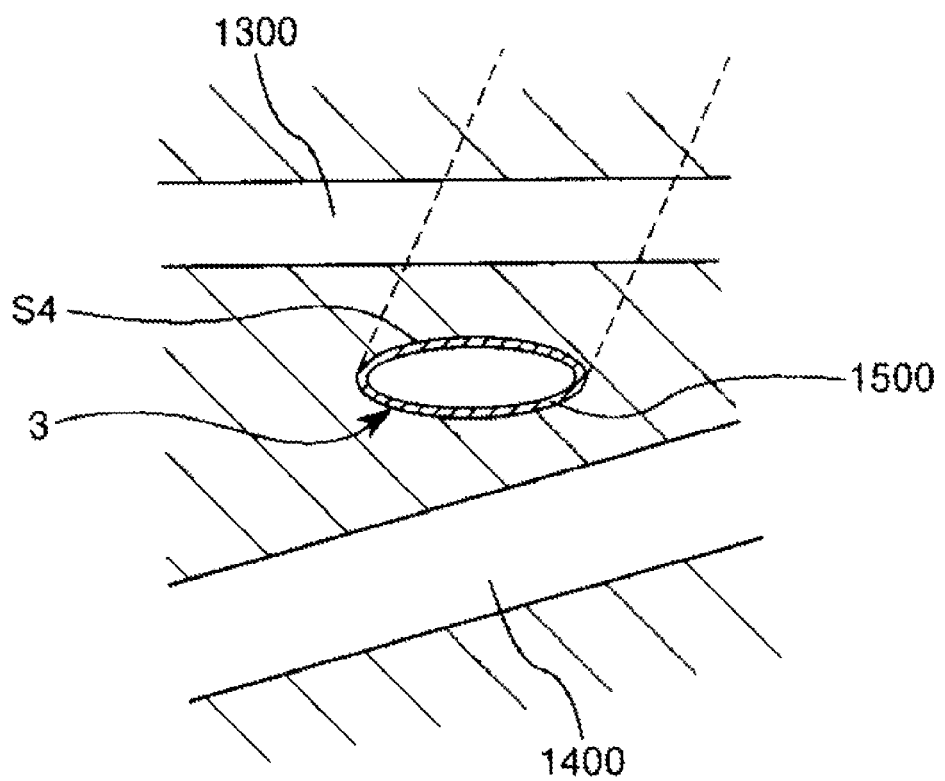

METHOD OF PLACING IMPLANT INDWELLING

CROSS-REFERENCES TO RELATED APPLICATIONS

This application claims priority to Japanese Application No. 2013-196172 filed on Sep. 20, 2013, the entire content of which is incorporated herein by reference.

TECHNICAL FIELD

The present disclosure relates to a method of placing an implant indwelling.

BACKGROUND DISCUSSION

In a patient suffering from urinary incontinence, for example, stress urinary incontinence, urine leakage (involuntary urination) can occur due to an abnormal pressure exerted during a normal exercise or by laughing, coughing, sneezing or the like. This can be attributable, for example, to loosening of the pelvic floor muscle, which is a muscle for supporting the urethra, caused by childbirth or the like.

For treatment of urinary incontinence, surgical therapy can be effective. For example, a tape-shaped implant called a "sling" can be placed indwelling in a body so as to support the urethra by the sling (for example, U.S. Pat. No. 6,911,003). In order to put a sling indwelling in the body, an operator incises a vagina with a surgical knife, dissects a biological tissue (living body tissue) between the urethra and the vagina, and provides communication between the exfoliated biological tissue site and an exterior through an obturator foramen by using a puncture needle or the like. Then, in such a state, the sling is placed indwelling in the body.

If a vaginal wall is once incised, however, there can be a fear that the sling might be exposed to an inside of the vagina via a wound caused by the incision. Also, there can be a fear that complications might occur which can be caused by an infection via the wound or the like. In addition, since the vaginal wall is incised, an invasiveness of the procedure can be rather great and a burden on a patient can be relatively heavy. In addition, there can be a fear that the urethra or the like might be damaged by a surgical knife in the course of the procedure by the operator, and also, there can be a fear that the operator himself might damage his fingertip by the surgical knife.

SUMMARY

In accordance with an exemplary embodiment, a method of placing an implant indwelling by which an implant can be placed indwelling in a living body with relatively low invasiveness is disclosed.

In accordance with an exemplary embodiment, a method of placing an implant indwelling in a living body is disclosed, the method can include forming an insertion hole in the living body, the insertion hole extending from a living body surface and passing an obturator foramen on one side and an obturator foramen on other side, an end portion of the insertion hole on the one side being opened in the living body surface, an end portion of the insertion hole on the other side being closed in relation to the living body surface, inserting a medical tube into the insertion hole prior to insertion of the implant, the medical tube permitting the implant to be inserted into the medical tube, inserting the implant into the medical tube inserted in the insertion hole and pulling the medical tube out of the insertion hole so that the implant is placed indwelling in the living body.

In accordance with an exemplary embodiment, the insertion hole passes between a urethra and a vagina.

In accordance with an exemplary embodiment, the insertion hole is formed by turning operation a turnable puncture needle having a needle tip by which to puncture the living body, and stopping the turning operation when the needle tip has passed the obturator on the one side and has passed the obturator on the other side.

In accordance with an exemplary embodiment, the implant is band-like in shape, and a length of the implant is shorter than a length of the insertion hole.

In accordance with an exemplary embodiment, the implant has an anchor portion that restricts longitudinal movement of a main body of the implant in a state where the medical tube has been pulled out and the implant has been thereby placed indwelling in the living body.

In accordance with an exemplary embodiment, an elongated operating member is put in abutment on the implant and is operated to move the implant forward in an inserting direction, at the time of inserting the implant into the medical tube.

In accordance with an exemplary embodiment, the operating member is provided at an intermediate portion in a longitudinal direction of the operating member with a marker that indicates a position of the operating member in the living body.

In accordance with an exemplary embodiment, a method of placing an implant indwelling in a living body is disclosed, the method can include forming an insertion hole in the living body, the insertion hole extending from a living body surface and passing an obturator foramen on one side and an obturator foramen on other side, an end portion of the insertion hole on the one side being opened in the living body surface, an end portion of the insertion hole on the other side being closed in relation to the living body surface, collectively inserting into the insertion hole both a medical tube permitting the implant to be inserted into the medical tube and the implant, the implant preliminarily inserted in the medical tube and pulling the medical tube out of the insertion hole so that the implant is placed indwelling in the living body.

In accordance with an exemplary embodiment, an insertion hole in which to insert an implant is so formed as to extend from a living body surface, to pass an obturator foramen on one side and an obturator foramen on the other side, and to have its one end portion opened in the living body surface and its other end portion closed in relation to the living body surface, which can help ensure that only one incised portion is formed in the body surface. Consequently, the burden on the patient can be relatively mitigated.

In accordance with an exemplary embodiment, an implant main body is disclosed, which can be shorter in length than the insertion hole, the implant can be placed indwelling in a deep position from the living body surface, which can also contributes to alleviation of burden on the patient.

For example, in the case where the implant main body has anchor portions for restricting movement of the implant main body in the longitudinal direction of the implant main body, in an indwelling state in which the implant main body is placed indwelling in a living body, the indwelling state can be maintained.

BRIEF DESCRIPTION OF THE DRAWINGS

FIGS. 4A and 4B illustrate a sheath possessed by the puncture apparatus shown in FIG. 1, wherein FIG. 4A is a perspective view and FIG. 4B is a sectional view taken along line 4B-4B in FIG. 4A.

FIGS. 7A and 7B illustrate a positional relationship between the puncture member and obturator foramens (pelvis), wherein FIG. 7A is a side view and FIG. 7B is a front view.

FIG. 8 is a partial magnified view of a vaginal insertion member possessed by the insertion instrument shown in FIG. 6.

FIG. 16 is a sectional view illustrating a posture of a puncture member relative to a urethra in the state shown in FIG. 14B.

DETAILED DESCRIPTION

FIGS. 1-19 are views showing a puncture apparatus to be used in a method of placing an implant indwelling according to a first exemplary embodiment of the present disclosure.

Figure 2:
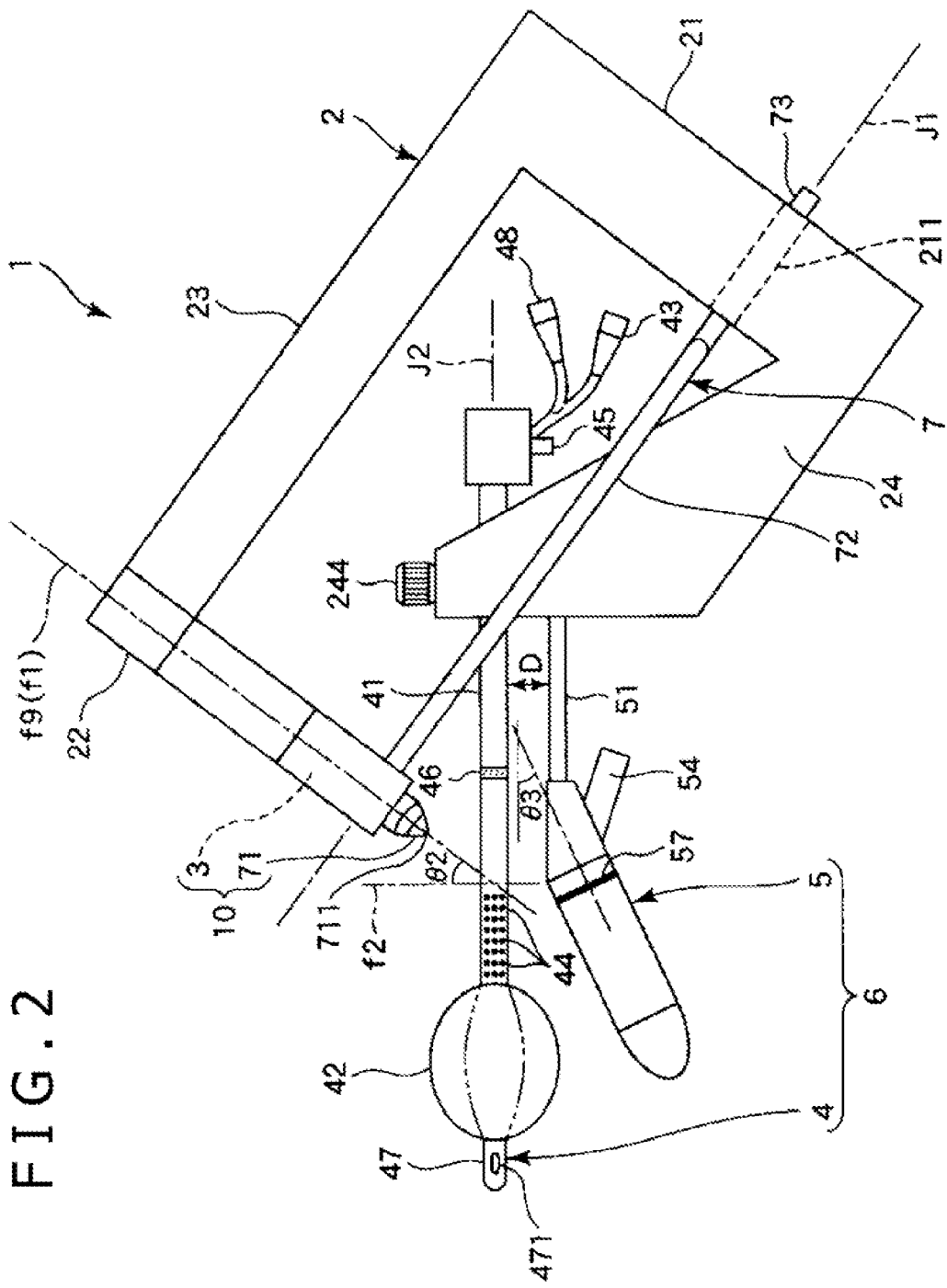
FIG. 2 is a side view of the puncture apparatus shown in FIG. 1.

In the following, for convenience of description, the left side in FIG. 2 and a needle tip in the drawings will be referred to as "distal (side)," the right side as "proximal (side)," the upper side as "upper (side)," and the lower side as "lower (side)." In addition, FIG. 2 shows the puncture apparatus in the state of being yet to be used, which state will hereinafter be referred to also as "initial state," for convenience of description. Further, a state wherein the puncture apparatus (insertion instrument) shown in FIG. 2 is mounted on a patient will be referred to also as "mounted state." In addition, in the drawings, the needle tip side and the forward side in regard of the traveling direction of the needle tip will be referred to also as "distal", and the side opposite to the needle tip side and the side opposite to the forward side in regard of the traveling direction of the needle tip will be referred to also as "proximal".

Figure 1:
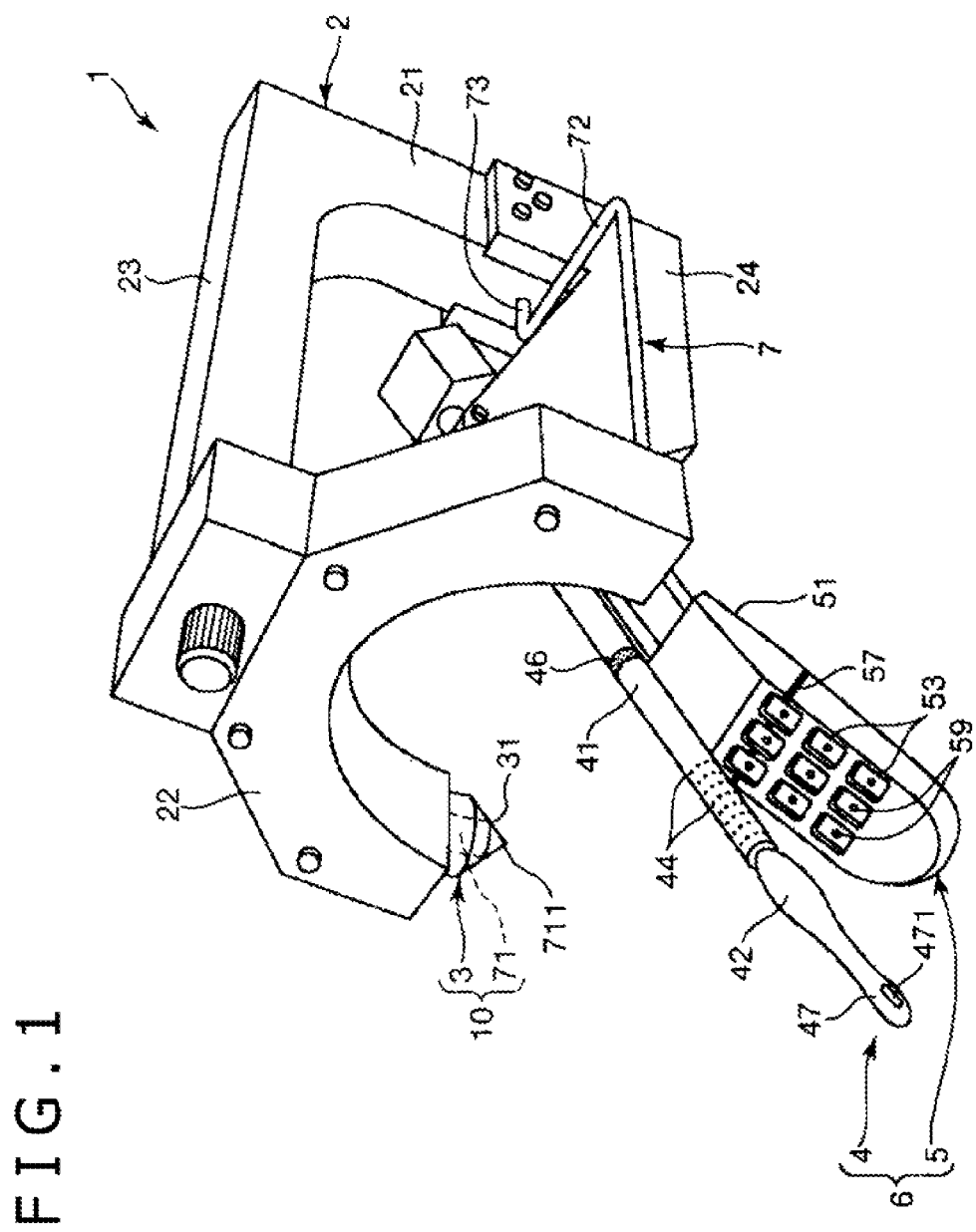
FIG. 1 is a perspective view showing a puncture apparatus to be used in a method of placing an implant indwelling according to a first exemplary embodiment of the present disclosure.

In accordance with an exemplary embodiment, a puncture apparatus 1 shown in FIGS. 1 and 2 can be an apparatus to be used for treatment of female urinary incontinence, for example, to be used in a process in which a biological tissue-supporting implant for treatment of urinary incontinence is implanted into a living body.

The puncture apparatus 1 can include a frame (support unit) 2, an implant 9, a sheath 3, a urethral insertion member 4, a vaginal insertion member 5, a puncture member 7, and an operating member 8. The sheath 3, the urethral insertion member 4, and the vaginal insertion member 5 can be supported on the frame 2, respectively. In the puncture apparatus 1, the urethral insertion member 4 and the vaginal insertion member 5 can constitute an insertion instrument 6.

Figure 3:
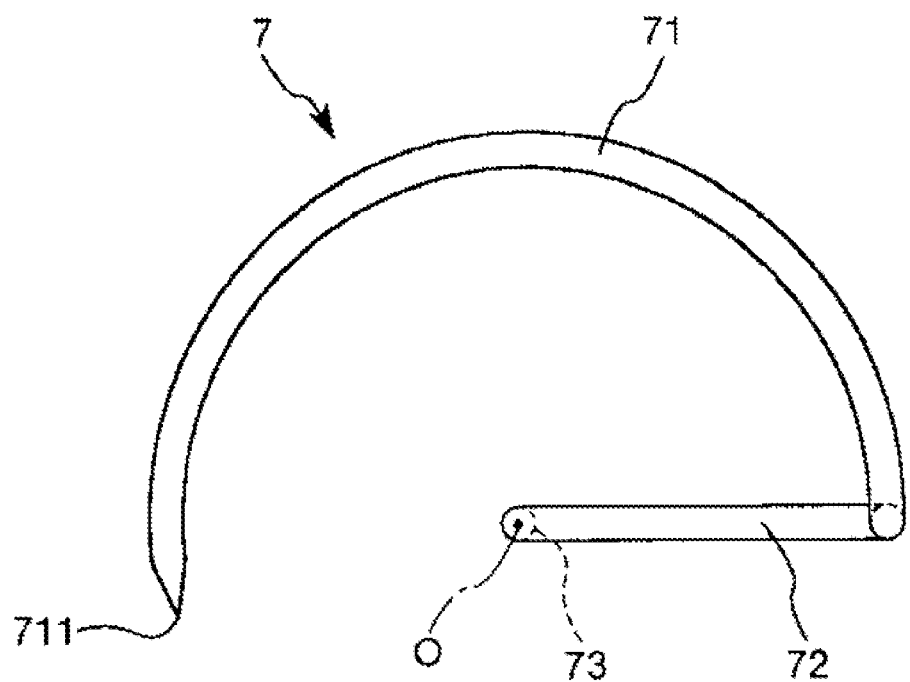
FIG. 3 is a plan view showing a puncture member possessed by the puncture apparatus shown in FIG. 1.

As shown in FIGS. 1 to 3, the puncture member 7 can include a puncture portion 71 having a puncture needle 711, a shaft portion 73; and an interlock portion 72 that interlocks the puncture portion 71 and the shaft portion 73 to each other. The puncture portion 71, the interlock portion 72, and the shaft portion 73 may be formed integrally, or, alternatively, at least one of these portions may be formed as a separate body in relation to the other portions.

The puncture portion 71 is a portion to be inserted in the sheath 3, and functions as a stylet that supports the sheath 3 from the inside. With the puncture portion 71 inserted in the sheath 3, the sheath 3 is connected to the puncture member 7, whereby operation of the sheath 3 by the puncture member 7 is enabled. Such a puncture portion 71 is in an arcuate shape corresponding to a shape of the sheath 3. A center angle of the puncture portion 71 is set in conformity with a center angle of the sheath 3. The needle tip 711 of the puncture portion 71 can be tapered off. The presence of the tapered needle tip 711 makes it possible to puncture a biological tissue, thereby forming an insertion hole 1500 in which to insert the implant 9.

The puncture portion 71 can be circular in cross-sectional shape, the puncture portion 71 may be flat-shaped in cross section. The flat shape is not limited. Examples of the flat shape applicable here can include not only ellipses but also rounded-cornered rhombuses, rounded-cornered rectangles (flat shapes), and spindle-like shapes enlarged (enlarged in diameter) at a central portion as compared with both end portions of the puncture portion 71.

The shaft portion 73 extends along an axis J1 which intersects a center O of the puncture portion 71 and which is orthogonal to a plane f1 that contains the puncture portion 71.

The interlock portion 72 interlocks a proximal portion of the puncture portion 71 and a distal portion of the shaft portion 73 to each other. In addition, the interlock portion 72 is substantially L-shaped, with a substantially rectangular bend at an intermediate portion of interlock portion 72. The interlock portion 72 can also function as a grasping portion to be grasped by an operator at the time of operating the puncture member 7.

The puncture member 7 can be configured to be higher than the sheath 3 in rigidity. The material constituting the puncture member 7 is not limited. Examples of the material applicable here can include various metallic materials such as stainless steels, aluminum, aluminum alloys, titanium, and titanium alloys.

The sheath 3 is configured by use of an elongate tube, and has a distal end opening 31 and a proximal end opening 32. The sheath 3 has an internal space in which an implant main body 91 can be inserted. In addition, a distal outer circumferential portion of the sheath 3 can have, for example, substantially the same taper as the taper of a distal portion of the puncture portion 71, which can help ensure that in a state in which the puncture portion 71 is inserted in the sheath 3, the distal outer circumferential portion of the sheath 3 and a distal outer circumferential portion of the puncture portion 71 form a continuous tapered surface.

Figure 4A:
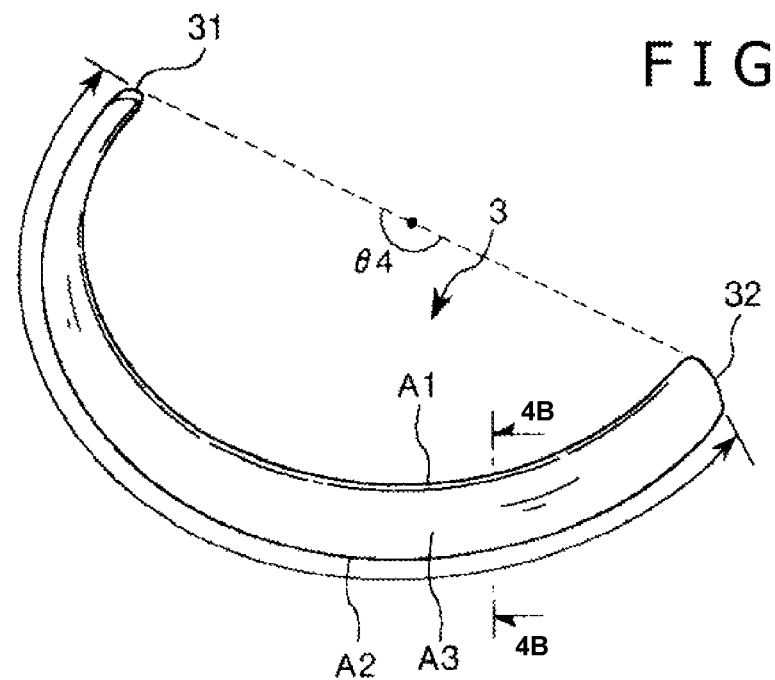
Figure 4B:
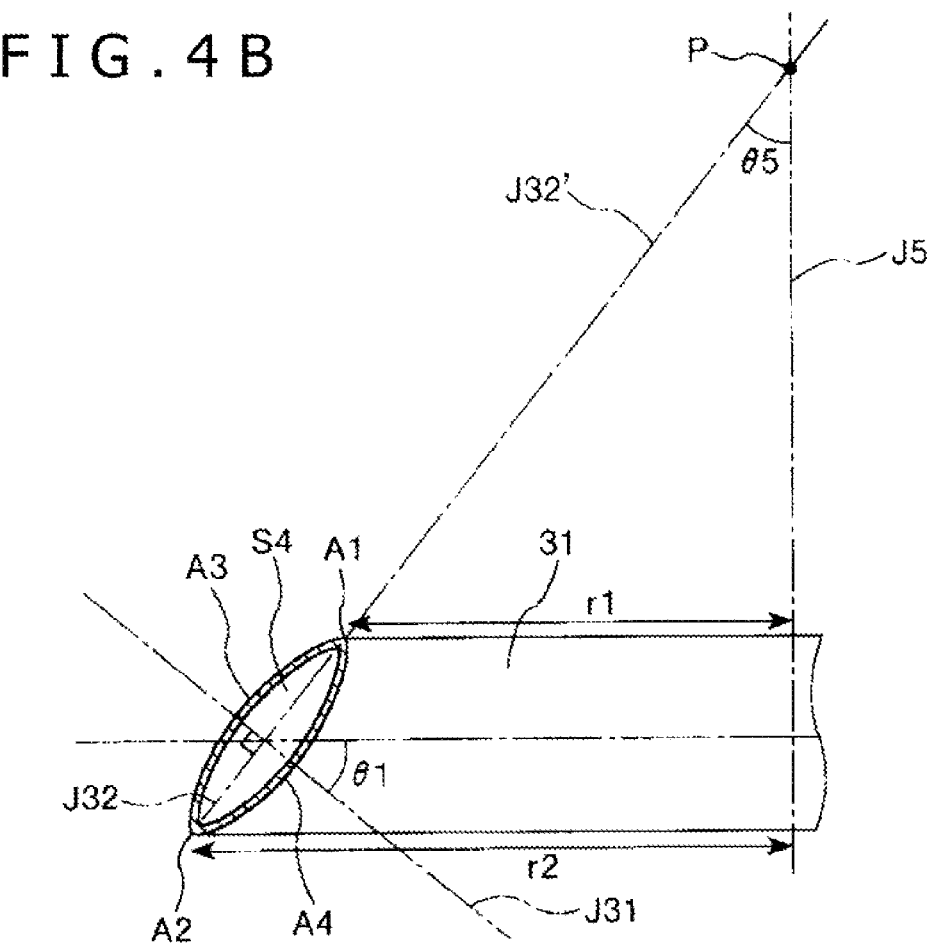

In addition, the sheath 3 can be in an arcuate curved shape, and can have a flat cross-sectional shape as shown in FIG. 4B. For example, the cross-sectional shape of the sheath 3 at an intermediate portion S4 in the longitudinal direction of the sheath 3 can be a flat shape, which can include a minor axis J31 and a major axis J32. As will be disclosed later, the implant main body 91 (implant 9) can be inserted in the sheath 3 (this state will hereinafter be referred to as "inserted state"). With the sheath 3 set in the flat shape, therefore, a posture of the implant main body 91 inside the sheath 3 can be controlled.

In accordance with an exemplary embodiment, a width (a length in a direction of the major axis J32) of the internal space of the sheath 3 can be designed to be approximately equal to a width of the implant main body 91, which can help ensure that even when the implant main body 91 is moved, a frictional resistance between the implant main body 91 and the internal space of the sheath 3 is lowered, and no unnecessary force is applied to the implant main body 91. Accordingly, the implant main body 91 can be disposed in a sufficiently expanded (spread) state in the inside of the sheath 3. The width (the length in the direction of the major axis J32) of the internal space of the sheath 3 may be shorter than the width of the implant main body 91, which helps ensure that the width of the sheath 3 is set smaller, so that a less invasive sheath 3 can be realized.

In accordance with an exemplary embodiment, the flat shape of the sheath 3 is not limited. Examples of the flat shape applicable here can include ellipses, sectionally convexed lens-like shapes, rounded-cornered rhombuses, rounded-cornered rectangles (flat shapes), and spindle-like shapes enlarged (enlarged in diameter) at a central portion as compared with both end portions of the sheath 3.

Hereinafter, for convenience of description, as shown in FIGS. 4A and 4B, an end portion located on an inner side (one end portion) in the direction of the major axis J32 will be referred to also as "inner circumferential portion A1," an end portion located on an outer side (other end portion) will be referred to also as "outer circumferential portion A2," a surface oriented upward will be referred to also as "front surface A3," and a surface oriented downward will be referred to also as "back surface A4."

When a plane containing both a center of an arc of the portion S4 and a center of the cross-sectional shape relative to the longitudinal direction of the sheath 3 (a plane containing a center axis of the sheath 3) is referred to as plane f9 and an angle formed between the plane f9 and the minor axis J31 at the portion S4 is referred to as inclination angle $\theta 1$, as shown in FIG. 4B, the inclination angle $\theta 1$ is preferably an acute angle. With the inclination angle $\theta 1$ set to be an acute angle, the implant 9 (described later) can be disposed substantially in parallel to the urethra, whereby the urethra can be supported relatively effectively. This effect will be described in detail later.

The inclination angle $\theta 1$ is not limited, insofar as it is an acute angle. The inclination angle $\theta 1$ can be, for example, about 20 to 60 degrees, preferably about 30 to 45 degrees, preferably about 35 to 40 degrees.

It can be preferable for the inclination angle $\theta 1$ to satisfy the above-mentioned numerical range throughout the whole region in the extending direction of the sheath 3. However, the above-mentioned effect can be displayed if only the inclination angle $\theta 1$ satisfies the above-mentioned numerical range at least in the portion S4 in the extending direction of the sheath 3. The "portion S4" refers to a region that can include a part located between the urethra and the vagina, at least, in a state in which the sheath 3 is puncturing a living body (a state wherein the sheath 3 is disposed in a living body).

The sheath 3 may be provided with a marker, at its proximal portion, for example, at its portion which is protruding to the outside of a living body in a state wherein the sheath 3 is disposed in the living body (a state as shown in FIG. 14), which can help ensure that by comparing the marker with a body surface H, the position of the sheath 3 in the living body can be checked.

In accordance with an exemplary embodiment, as shown in FIG. 4B, the sheath 3 can be so formed that the major axis J32 is inclined against a center axis J5 of the arc and that the center axis J5 of the arc and an extension line J32' of the major axis J32 have an intersection P. In this case, an angle $\theta 5$ formed between the center axis J5 and the extension line J32' is equal to the inclination angle $\theta 1$. For example, it can be said that the sheath 3 has the inner circumferential portion A1 located at an inner circumferential edge (in plan view as viewed from the direction of the center axis J5 of the sheath 3) and having a minimum radius of curvature, r1, and also has the outer circumferential portion A2 located at an outer circumferential edge (in the plan view) and having a maximum radius of curvature, r2, and that the inner circumferential portion A1 and the outer circumferential portion A2 are located to be spaced (deviated) from each other along the direction of the center axis J5, as shown in FIG. 4B.

In accordance with an exemplary embodiment, in the case where at least a portion in the longitudinal direction, of the puncture portion 71, is flat-shaped in cross section correspondingly to the lumen of the sheath 3, the flat shapes of these corresponding portions overlap each other in a state in which the puncture portion 71 is inserted in the sheath 3, which overlap helps ensure that the sheath 3 is restricted from rotating relative to the puncture portion 71, about the axis thereof.

In accordance with an exemplary embodiment, a center angle θ4 of the sheath 3 is not limited, and can be set, as necessary, according to various conditions. In this case, as will be disclosed later, the center angle θ4 is so set that the needle tip 711 can enter a body via a patient's inguinal region on one side, pass between the urethra and the vagina and protrude to the outside of the body via an inguinal region on the other side. For example, the center angle θ4 can be, for example, in the range of about 100 to 180 degrees, preferably about 120 to 160 degrees, and more preferably about 130 to 150 degrees.

The material constituting the sheath 3 can be, for example, a material being rigid to such an extent that it can maintain the shape and an internal space (lumen) of the sheath 3 in the state of being inserted in a body. Examples of such rigid material applicable here include various resin materials such as polyethylene, polyimides, polyamides, polyester elastomers, polypropylene, etc. and various metallic materials such as stainless steels, aluminum, aluminum alloys, titanium, and titanium alloys. In accordance with an exemplary embodiment, instead of adopting rigid materials for constituting the sheath 3 and the needle tip 711, other materials than rigid materials may also be adopted, in which case a wall of the sheath 3 or the needle tip 711 is reinforced with a reinforcement member, whereby the properties as above-mentioned are attained. For example, a high-strength braiding may be embedded in the wall of the sheath 3 or the needle tip 711, whereby the shape and the internal space of the sheath 3 or the needle tip 711, in the state of being inserted in a body, can be maintained. Another example of the reinforcement member is a spiral body, which may be embedded in the wall of the sheath 3, whereby the sheath 3 can have flexibility while retaining the internal space to such an extent that an inserted body can be slid into the sheath 3.

In accordance with an exemplary embodiment, the sheath 3 can be, for example, light-transmitting so that the inside of the sheath 3 can be externally visible.

The sheath 3 as above-described and the puncture portion 71 to be inserted in the sheath 3 constitute a medical tube assembly 10, and, in this puncture apparatus 1, the use of the sheath 3 and the puncture portion 71 is started in the state in which they have been assembled into the medical tube assembly 10.

In accordance with an exemplary embodiment, there may be provided a mechanism for restricting a limit of insertion of the puncture portion 71 into the sheath 3. Examples of this restricting mechanism include a flange-shaped stopper provided at a proximal portion of the puncture portion 71, which helps ensure that when a proximal portion of the sheath 3 comes into abutment on the stopper, the limit of insertion is thereby restricted. Furthermore, at the time of puncturing a living body, the sheath 3 can be relatively prevented from being moved proximally in relation to the puncture portion 71 by puncturing resistance.

In accordance with an exemplary embodiment, the restricting mechanism can be composed essentially of the interlock portion 72, which helps eliminate the need to separately provide a member as the restricting mechanism.

The frame 2 can turnably hold the puncture member 7 on which the sheath 3 is mounted. The frame 2 can have a function of determining a puncture route for the needle tip 711 at the time of punting a biological tissue by the sheath 3. For example, the frame 2 determines a positional relationship between the sheath 3, the urethral insertion member 4, and the vaginal insertion member 5 in such a manner that when a biological tissue is punctured by the sheath 3, the needle tip 711 passes between the urethral insertion member 4 and the vaginal insertion member 5 without colliding against any of the insertion members 4 and 5.

As shown in FIGS. 1 and 2, the frame 2 can include a bearing portion 21 for bearing the shaft portion 73 of the puncture member 7, a guide portion (holding portion) 22 for guiding the sheath 3, an interlock portion 23 interlocking the bearing portion 21 and the guide portion 22 to each other, and a fixing portion 24 to which the insertion instrument 6 is fixed.

The bearing portion 21 can be located on the proximal end in the puncture apparatus 1, and extends in a direction substantially orthogonal to the axis J1. The bearing portion 21 is formed with a through-hole 211 in a position on the axis J1, and the shaft portion 73 is turnably inserted in the through-hole 211, which can help ensure that the puncture member 7 is supported on the frame 2 in a state of being turnable about the axis J1.

In accordance with an exemplary embodiment, the guide portion 22 can be located on the distal end in the puncture apparatus 1, and can be disposed opposite to the bearing portion 21. The guide portion 22 can be formed with a roughly C-shaped guide groove for accommodating the sheath 3 and guiding the sheath 3.

The interlock portion 23 can be interlocking the bearing portion 21 and the guide portion 22 to each other. In addition, the interlock portion 23 is in the form of a bar extending substantially in parallel to the axis J1. The interlock portion 23 functions also as a grasping portion, to allow an operator to use the puncture apparatus 1 by grasping the interlock portion 23.

Figure 5:
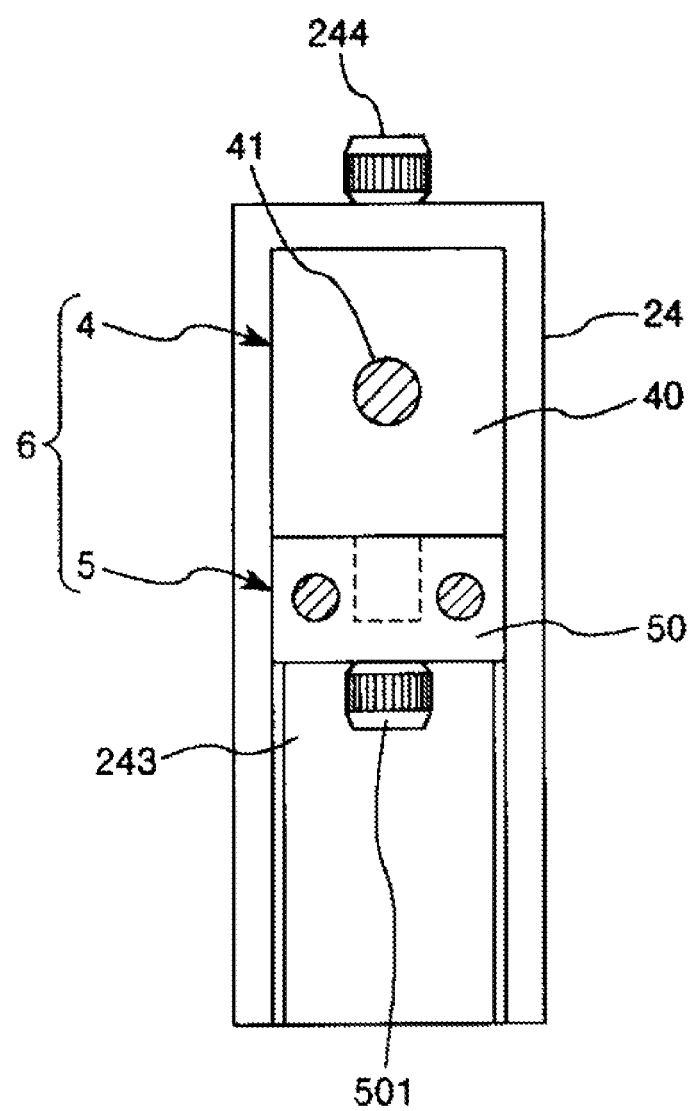
FIG. 5 is a plan view showing a fixing portion of a frame possessed by the puncture apparatus shown in FIG. 1.

The fixing portion 24 is disposed opposite to the interlock portion 23, with the axis J1 interposed therebetween. As shown in FIG. 5, the fixing portion 24 is provided with a recess 243 in which to fit a support part 60 (described later) of the insertion instrument 6, and a male screw 244. With the support part 60 fitted in the recess 243 and with the male screw 244 fastened into a female screw (not shown) in the support part 60, the insertion instrument 6 can be fixed to the fixing portion 24.

Figure 6:
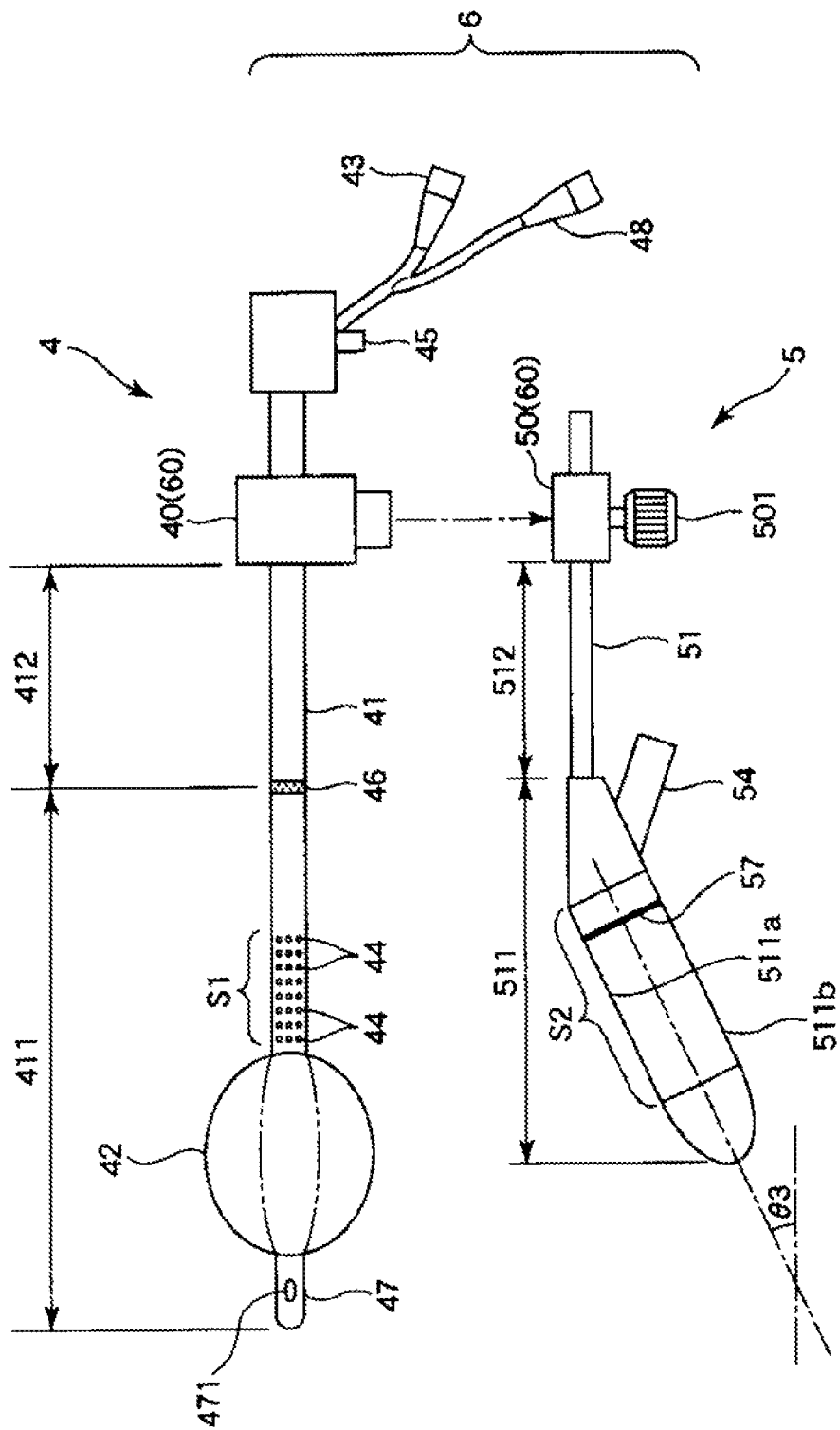
FIG. 6 is a side view of an insertion instrument possessed by the puncture apparatus shown in FIG. 1.

As shown in FIGS. 1, 2, and 6, the insertion instrument 6 can include a urethral insertion portion (second insertion portion) 41 to be inserted into a urethra, a vaginal insertion portion (first insertion portion) 51 to be inserted into a vagina, and a support part 60 supporting the urethral insertion portion 41 and the vaginal insertion portion 51. As has been disclosed above, the insertion instrument 6 is composed essentially of the urethral insertion member 4 and the vaginal insertion member 5. The urethral insertion member 4 has the urethral insertion portion 41, and the vaginal insertion member 5 has the vaginal insertion portion 51. In addition, the support part 60 can includes a support portion 40, which is possessed by the urethral insertion member 4 and supports the urethral insertion portion 41; and a support portion 50, which is possessed by the vaginal insertion member 5 and supports the vaginal insertion portion 51. In the insertion instrument 6, the urethral insertion member 4 and the vaginal insertion member 51 can be freely detachable by way of the support portions 40 and 50, respectively.

In accordance with an exemplary embodiment, the urethral insertion member 4 can include the elongated urethral insertion portion 41 whose portion ranging from a distal end to an intermediate portion of the urethral insertion portion 41 is to be inserted into a urethra, and the support portion 40 which supports the urethral insertion portion 41. In the following, for convenience of description, that portion which is located inside the urethra (inclusive of a bladder) in the mounted state will be referred to also as "insertion portion 411," whereas that portion which is exposed via a urethra orifice to the outside of the body in the mounted state and which ranges to the support portion 40 will be referred to also as "non-insertion portion 412."

The urethral insertion portion 41 can be in the shape of a tube with its distal end rounded. In addition, the insertion portion 411 can be provided at its distal portion with an inflatable and deflatable balloon 42 and a urine drain portion 47. The balloon 42 can function as a restriction portion for restricting the position in an axial direction of the urethral insertion member 4 in the inside of the urethra. For example, when the puncture apparatus 1 is used, the balloon 42 is inflated after inserted into a patient's bladder. Then, with the balloon 42 caught on a bladder neck, the position of the urethral insertion member 4 relative to the bladder and the urethra can be fixed. In accordance with an exemplary embodiment, the urine drain portion 47 can be used for draining urine present inside the bladder.

The balloon 42 extends through the inside of the urethral insertion portion 41, to be connected to a balloon port 43 provided at a proximal portion of the urethral insertion portion 41. A balloon-inflating instrument such as a syringe can be connected to the balloon port 43. When a working fluid (a liquid such as physiological salt solution, or a gas or the like) is supplied from the balloon-inflating instrument into the balloon 42, the balloon 42 is inflated. On the contrary, when the working fluid is drawn out of the balloon 42 by the balloon-inflating instrument, the balloon 42 is deflated. In FIG. 6, the balloon 42 in its deflated state is drawn in two-dot chain line, whereas the balloon 42 in its inflated state is drawn in solid line.

In accordance with an exemplary embodiment, the urine drain portion 47 can be provided with a drain hole 471 providing communication between the inside and the outside of the urine drain portion 47. In addition, the urine drain portion 47 extends through the inside of the urethral insertion portion 41, to be connected to a urine drain port 48 provided at a proximal portion of the urethral insertion portion 41. Therefore, the urine introduced through the drain hole 471 into the urine drain portion 47 can be drained via the urine drain port 48.

The balloon 42 and the urine drain portion 47 can be configured by use of a double lumen, for example.

In accordance with an exemplary embodiment, the insertion portion 411 can be formed with a plurality of suction holes 44 at an intermediate portion of the insertion portion 411. The plurality of suction holes 44 can be laid out over the whole range in the circumferential direction of the urethral insertion portion 41. Each of the suction holes 44 can be connected to a suction port 45 provided at the proximal portion of the urethral insertion portion 41, via the inside of the urethral insertion portion 41. A suction device such as a pump can be connected to the suction port 45. When the suction device is operated in a state wherein the urethral insertion portion 41 is inserted in the urethra, a urethral wall can be sucked and fixed onto the urethral insertion portion 41. When the urethral insertion portion 41 is pushed in toward the distal end (toward the inside of the body) under this condition, the urethra is also pushed in together with the urethral insertion portion 41. As a result, for example, the bladder can be shifted to such a position as not to overlap with a puncture route for the sheath 3, whereby the puncture route for the sheath 3 can be secured. Therefore, puncturing by the sheath 3 can be carried out relatively accurately and safely. It is to be noted that the number of the suction holes 44 is not limited, for instance, the number may be one. In addition, the layout of the suction holes 44 is not limited, for example, the suction holes 44 may be formed in only a part of the range in the circumferential direction of the urethral insertion portion 41.

In addition, at the boundary between the insertion portion 411 and the non-insertion portion 412, there is provided a marker 46 with which to check a depth of insertion of the urethral insertion portion 41 into the urethra. When the urethral insertion portion 41 is inserted in the urethra and the balloon 42 is located inside the bladder, the marker 46 is located at the urethral orifice, which helps permit easy checking of the depth of insertion of the insertion portion 411 into the urethra. The marker 46 is necessary only to be externally visible, and can be composed essentially of, for example, a colored portion, a recessed and projected portion, or the like. Incidentally, a graduation with indications of distance from the distal end of the urethral insertion portion 41 may be provided, in place of the marker 46.

A length of the insertion portion 411 is not limited, and may be set, as necessary, according to a length of the urethra and a shape of the bladder of the patient, or the like. The length of the insertion portion 411 can be, for example, about 50 to 100 mm, in view of the fact that a length of a female urethra is generally about 30 to 50 mm.

A length of the non-insertion portion 412 (the spacing between the urethral orifice and the support portion 40) is limited. For example, the length should not be more than about 100 mm, for example, preferably in the range of about 20 to 50 mm. By such a setting, the length of the non-insertion portion 412 can be made appropriate, which promises enhanced operability. If the length of the non-insertion portion 412 exceeds the just-mentioned upper limit, a center of gravity of the puncture apparatus 1 would, depending on the configuration of the frame 2 or the like factors, be largely deviated from the patient, possibly leading to a lowered stability of the puncture apparatus 1 in the mounted state.

The material constituting the urethral insertion member 4 is not limited. Examples of the material applicable here include various metallic materials such as stainless steels, aluminum, aluminum alloys, titanium, titanium alloys, etc. and various resin materials.

Here, an inclination angle θ2 of the plane f9 relative to a plane f2 orthogonal to an axis J2 of the urethral insertion portion 41 can be, for example, about 20 to 60 degrees, preferably about 30 to 45 degrees, and more preferably about 35 to 40 degrees. In accordance with an exemplary embodiment, the sheath 3 can be, for example, set indwelling in the living body so that the angle formed between the plane f9 and a plane orthogonal to the axis of the urethra is about 20 to 60 degrees, more preferably about 30 to 45 degrees, and further preferably about 35 to 40 degrees. Such a setting can make the puncturing by the sheath 3 rather easy to perform and can shorten the distance (or length) of the puncture by the sheath 3.

Figure 7A:
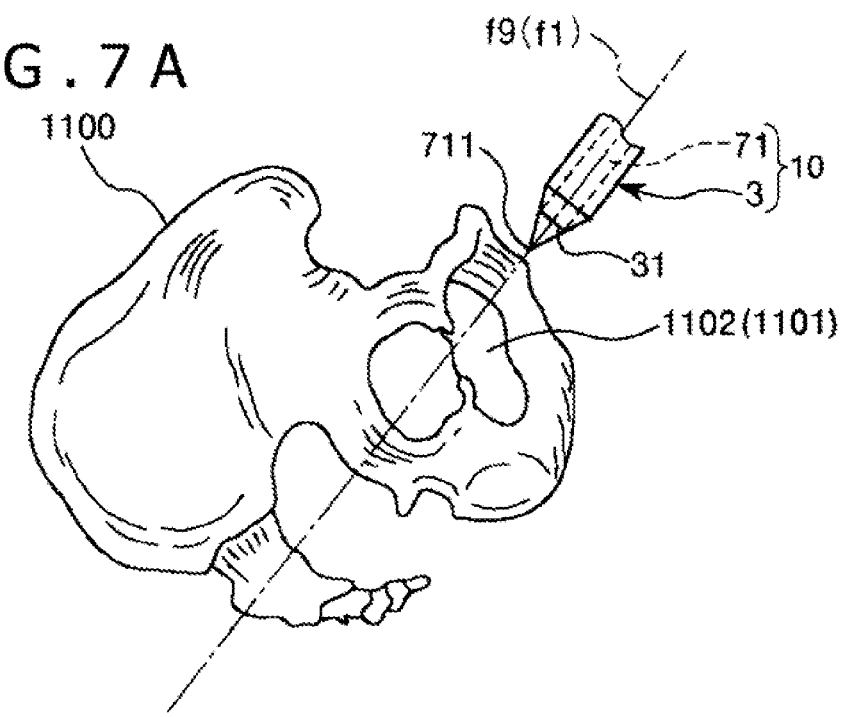
Figure 7B:
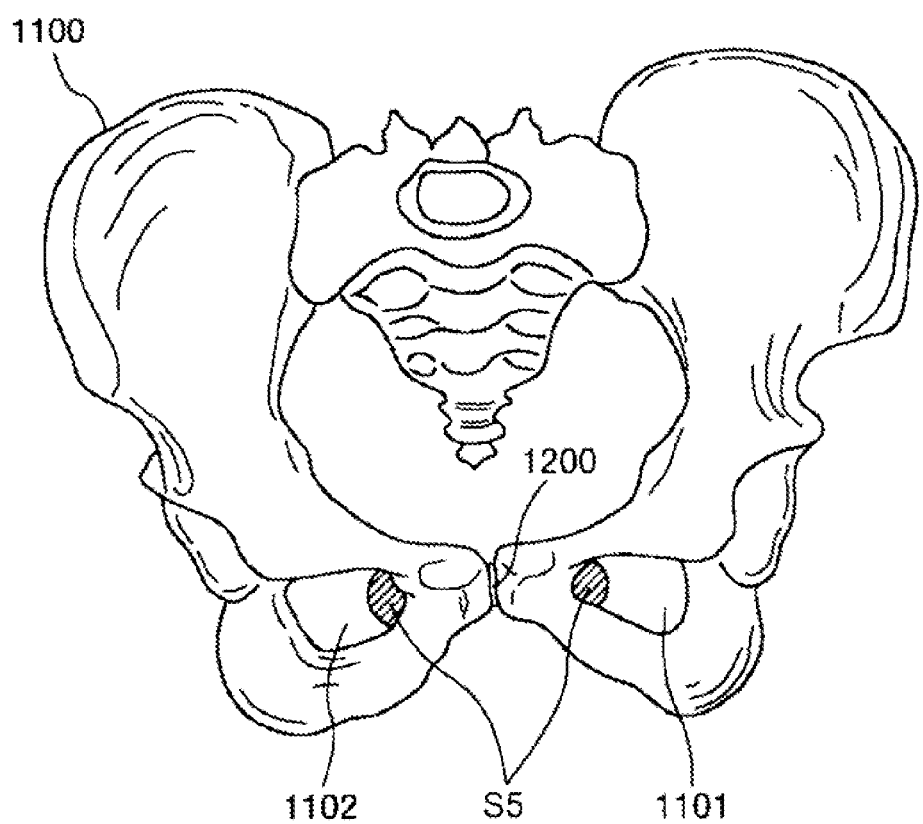

In accordance with an exemplary embodiment, as shown in FIG. 7A, setting the inclination angle θ2 to within the above-mentioned range helps ensure that the sheath 3 can capture the left and right obturator foramens 1101 and 1102 of a pelvis 1100 wider on a planar basis, so that a wide puncturing space for the sheath 3 can be secured. For example, in a condition where a patient is put in a predetermined posture (lithotomy position), puncturing by the sheath 3 can be performed in a direction comparatively nearer to a perpendicular direction relative to the obturator foramens 1101 and 1102. Therefore, the puncturing by the sheath 3 can be carried out relatively easily. In addition, since the puncturing by sheath 3 is performed in a direction comparatively nearer to the perpendicular direction relative to the obturator foramens 1101 and 1102, it can help ensure that the sheath 3 passes through a shallow part of tissue, so that the sheath 3 can cross a region between the left and right obturator foramens 1101 and 1102 by passing a short distance. Accordingly, as shown in FIG. 7B, the sheath 3 can be passed through those regions of the obturator foramens 1101 and 1102 which are near a pubic symphysis 1200, preferably, through safety zones S5. Since the safety zones S5 are regions where there are few nerves and blood vessels the damage to which is to be obviated, puncturing by the sheath 3 can be performed relatively safely. The result is minimal invasiveness, whereby burden on the patient can be suppressed. Thus, with the inclination angle θ2 set to within the above-mentioned range, puncturing of a patient by the sheath 3 can be performed appropriately. For example, by puncturing at the above-mentioned angle, it is facilitated to aim at a tissue between a middle-part urethra (which refers to an intermediate part in a lengthwise direction of the urethra) and the vagina. A position between the middle-part urethra and the vagina is a position suitable as a site where to embed the implant 9 for treatment of urinary incontinence.

For example, in the case where the inclination angle θ2 is less than the aforementioned lower limit or in excess of the aforementioned upper limit, there may arise an issue in that, depending on the individual differences concerning the patient or the posture during the procedure or the like factors, the sheath 3 cannot capture the obturator foramens 1101 and 1102 wide on a planar basis or the puncture route cannot be made sufficiently short.

For example, the puncturing can be conducted in a condition where either one or both of the urethra and the vagina can be positionally so shifted as to be pushed toward the inside of the body. Such an operation permits easy puncturing of the tissue between the middle-part urethra and the vagina. The method for pushing in either one of the urethra and the vagina toward the inside of the body may be, for example, a method in which the urethral insertion member 4 and/or the vaginal insertion member 5 is inserted into an appropriate position, then, in this condition, the urethra and/or the vagina is sucked by the suction holes 44 and 59 (described later) possessed by these members 4 and 5, and thereafter the urethral insertion member 4 and/or the vaginal insertion member 5 is further moved toward the inside of the body along the axis thereof until reaching a predetermined position. In the condition where at least one of the urethra and the vagina has thus been positionally shifted so as to be pushed in toward the inside of the body, the sheath 3 is made to puncture the living body perpendicularly to the left and right obturator foramens 1101 and 1102 of the pelvis, whereby a passage can be formed in a position suited to implanting of the implant 9.

In accordance with an exemplary embodiment, a setting can be made to cause an orbital path of the sheath 3 to pass the safety zones S5 of the left and right obturator foramens 1101 and 1102 of the pelvis, at least one of the urethra and the vagina is positionally shifted toward the inside of the body so as to locate the orbital path between the middle-part urethra and the vagina, and puncturing is performed along the orbital path of the sheath 3, thereby forming the passage.

As shown in FIGS. 1, 2, and 6, the vaginal insertion member 5 can include the elongated vaginal insertion portion (first insertion portion) 51 whose portion from a distal end to an intermediate portion of vaginal insertion portion 51 is inserted into a vagina, and the support portion 50 supporting the vaginal insertion portion 51. For example, in the following, for convenience of description, that portion of the vaginal insertion portion 51 which is located in the vagina in the mounted state will be referred to also as "insertion portion 511," and that portion of the vaginal insertion portion 51 which is exposed via a vaginal orifice to the outside of the body in the mounted state and which ranges to the support portion 50 will be referred to also as "non-insertion portion 512."

The insertion portion 511 can be elongated. In addition, the insertion portion 511 can extend at an inclination relative to the insertion portion 411 so that the insertion portion 511 is spaced from the insertion portion 411 on the distal end. With the insertion portion 511 inclined relative to the insertion portion 411, a positional relationship between the insertion portions 411 and 511 can be set closer to the positional relationship between the urethra and the vagina, as compared with the case where the insertion portion 511 is not inclined in this way. In the mounted state, therefore, the puncture apparatus 1 can be held onto the patient stably, and burden on the patient is mitigated. An inclination angle θ3 of the insertion portion 511 relative to the insertion portion 411 is not limited, for example, the inclination angle θ3 can be, for example, about 0 to 45 degrees, more preferably about 0 to 30 degrees, which helps enable the above-mentioned effect to be conspicuously displayed. For example, in the case where the inclination angle θ3 is less than the aforementioned lower limit or in excess of the aforementioned upper limit, there may arise an issue in that, depending on individual differences concerning the patient or the posture during the procedure or the like factors, the urethra and/or the vagina may be deformed unnaturally in the mounted state, possibly hampering the puncture apparatus 1 from being stably held.

As shown in FIG. 8, the insertion portion 511 can be in a flat shape collapsed in the vertical direction of the puncture apparatus 1 (in an array direction of the urethra and the vagina). In addition, the insertion portion 511 can have a central portion having a substantially constant width and a somewhat rounded distal portion. A length L2 of the insertion portion 511 is not limited, and can be, for example, about 20 to 100 mm, and preferably about 30 to 60 mm. A width W1 of the insertion portion 511 is not limited, and can be, for example, about 10 to 50 mm, and preferably about 20 to 40 mm. In accordance with an exemplary embodiment, a thickness of the insertion portion 511 is not limited, and can be, for example, about 5 to 25 mm, and preferably about 10 to 20 mm. Set to have such length, width, and thickness, the insertion portion 511 can be suited in shape and size to ordinary vaginas. Therefore, the stability of the puncture apparatus 1 in the mounted state can be enhanced, and burden on the patient is relatively alleviated.

In addition, an upper surface (a surface on the urethral insertion portion 41 side) 511a of the insertion portion 511 can be formed with a plurality of bottomed recesses. The number of recesses 53 is not limited, for example, the number may be one. In accordance with an exemplary embodiment, each recess 53 can be provided with a single suction hole 59 in its bottom surface. Each suction hole 59 is connected to a suction port 54 provided at a proximal portion of the insertion portion 511, through the inside of the insertion portion 511. The suction port 54 is so provided as to be located in the outside of the living body in the mounted state. A suction device such as a pump can be connected to the suction port 54. When the suction device is operated in the condition where the insertion portion 511 is inserted in a vagina, an anterior wall of vagina, which is an upper surface of a vaginal wall, is sucked and fixed onto the insertion portion 511. When the vaginal insertion portion 51 with the vaginal wall sucked and fixed thereon is pushed toward the distal end (toward the inside of the body), the vaginal wall can be pushed in together with the vaginal insertion portion 51. Therefore, it is possible to put in good order the layout and shape of the vaginal wall, to secure a puncture route for the sheath 3, and to perform puncturing by the sheath 3 relatively accurately and safely.

A region S2 in which the plurality of recesses 53 are formed is disposed opposite to a region S1. A needle tip of the sheath 3 passes between these regions S1 and S2. Since a lower surface of the urethral wall is sucked onto the insertion portion 411 in the region S1 and the anterior wall of vagina is sucked onto the insertion portion 511 in the region S2, as disclosed above, the urethral wall and the vaginal wall can be spaced apart from each other between the regions S1 and S2. By causing the sheath 3 to pass such a region, therefore, the puncturing by the sheath 3 can be performed relatively safely.

Figure 9A:
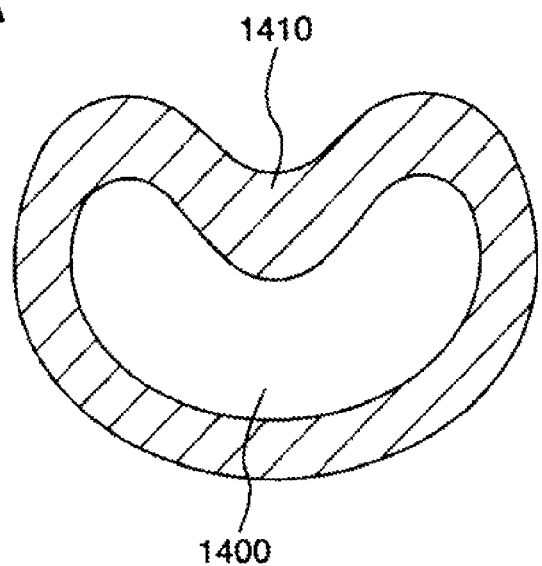
FIG. 9A is a sectional view showing an example of a shape of a vaginal wall.
Figure 9B:
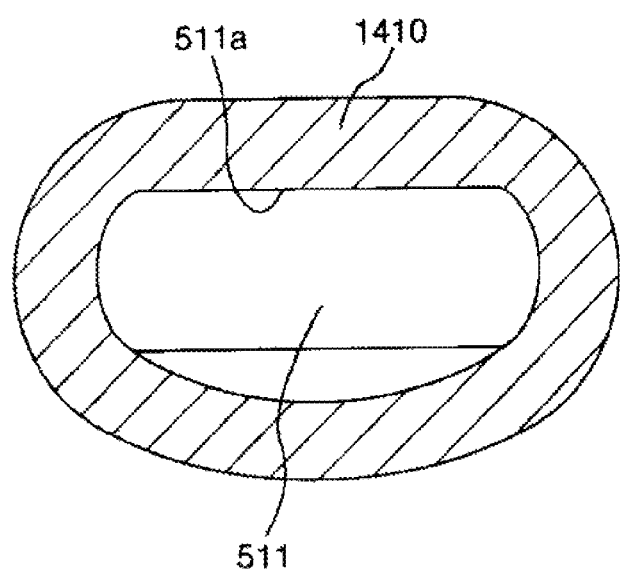
FIG. 9B is a sectional view showing a state in which a vaginal insertion portion has been inserted in an inside of the vagina shown in FIG. 9A.

The region S2 ranges over substantially the whole region in a width direction of the upper surface 511a. A width W2 of the region S2 is not limited, and can be, for example, about 9 to 49 mm, and preferably about 19 to 39 mm, which helps enable the anterior wall of vagina to be reliably sucked onto the insertion portion 511, without being much influenced by the shape of the vaginal wall. For example, in some patients, the vagina 1400 may be so shaped that part of an anterior wall of vagina, 1410, is hanging down into the inside of the vagina, as shown in FIG. 9A. Even in such a case, setting the width W2 to within the above-mentioned range helps ensure that not only the hanging-down portion but also the portions on both sides of the hanging-down portion can be sucked, as shown in FIG. 9B. Therefore, the anterior wall of vagina can be reliably spaced from the urethra, without being affected by the shape of the vagina. For example, in this exemplary embodiment, the insertion portion 511 is flat-shaped, so that the anterior wall of vagina can be so sucked as to be spaced apart from the urethra. Consequently, the biological tissue between the urethral wall and the vaginal wall can be expanded (spread).

In addition, as shown in FIG. 11, the insertion portion 511 is provided with a marker (puncture position checking portion) 57 with which a puncture route for the puncture apparatus 1 can be checked. For example, the puncture apparatus 1 can be so fixed as to puncture a region (biological tissue) between the vaginal wall present on an upper side of the position where the marker 57 is located and the urethral wall. Therefore, operability and safety of the insertion instrument 6 can be relatively enhanced. The marker 57 is provided at least on a lower surface 511b of the insertion portion 511. The lower surface 511b is a surface which is oriented toward the vaginal orifice and can be visually confirmed by the operator via the vaginal orifice, in a state wherein the insertion portion 511 is inserted in the vagina 1400. With the marker 57 provided on the lower surface 511b, therefore, the puncture route for the puncture apparatus 1 can be reliably checked. In addition, a depth of insertion of the insertion portion 511 into the vagina can also be checked. It is to be noted that the marker 57 is necessary only to be externally visible, and can be configured by use of, for example, a colored portion, a recessed and projected portion, or the like.

The non-insertion portion 512 is in the shape of a thin bar, which can extend substantially in parallel to the urethral insertion portion 41. A spacing D between the non-insertion portion 512 and the urethral insertion portion 41 is not limited, and can be, for example, about 5 to 40 mm, correspondingly to the spacing between the urethral orifice and the vaginal orifice in common women.

A length of the non-insertion portion 512 (a spacing between the vaginal orifice and the support portion 50) is not limited, and can be, for example, not more than about 100 mm, preferably in the range of about 20 to 50 mm, which helps permit the non-insertion portion 512 to be appropriate in length, leading to enhanced operability. If the length of the non-insertion portion 512 exceeds the just-mentioned upper limit, the center of gravity of the puncture apparatus 1 would, depending on the configuration of the frame 2 or the like factors, be largely deviated from the patient, possibly leading to a lowered stability of the puncture apparatus 1 in the mounted state.

The support portion 50 is provided with a male screw 501. With the male screw 501 fastened into a female screw (not shown) formed in the support portion 40, the support portions 40 and 50 are fixed to each other.

The material constituting the vaginal insertion member 5 is not limited. Examples of the material applicable here include various metallic materials such as stainless steels, aluminum, aluminum alloys, titanium, titanium alloys, etc. and various resin materials, like the examples of the material for the urethral insertion member 4.

In accordance with an exemplary embodiment, while the urethral insertion member 4 and the vaginal insertion member 5 constituting the insertion instrument 6 are freely detachable in the puncture apparatus 1, this configuration is not limited. For example, a configuration may be adopted in which the urethral insertion member 4 and the vaginal insertion member 5 are non-detachable.

In addition, while the urethral insertion portion 41 is fixed to the support portion 40 in the puncture apparatus 1, this configuration is not limited. For example, a configuration may be adopted wherein the urethral insertion portion 41 can be selectively switched between a state of being fixed to the support portion 40 and a state of being slidable in the axial direction relative to the support portion 40. For example, a configuration may be adopted wherein untightening of a screw provided on the support portion 40 permits the urethral insertion portion 41 to be slid relative to the support portion 40, whereas tightening the screw renders the urethral insertion portion 41 fixed to the support portion 40. This configuration helps enable regulation of the length of the non-insertion portion 412, which can make the insertion instrument 6 user-friendly. It is to be noted that this also applies to the vaginal insertion portion 51.

In accordance with an exemplary embodiment, while the members are fixed to the frame 2 so that the inclination angle θ2 will be constant in the puncture apparatus 1, this configuration is not limited. Thus, the inclination angle θ2 may be variable, which helps permit the inclination angle θ2 to be controlled according to the patient to be treated, which makes the puncture apparatus 1 better in utility.

In accordance with an exemplary embodiment, the implant 9 can be an embeddable (implantable) instrument for treatment of female urinary incontinence, specifically, an instrument for supporting a urethra 1300. For example, when the urethra 1300 tends to move toward the vagina 1400 side, the implant 9 can support the urethra 1300 in such a manner as to restrict its movement in a direction of coming away from the vagina 1400.

Figure 10:
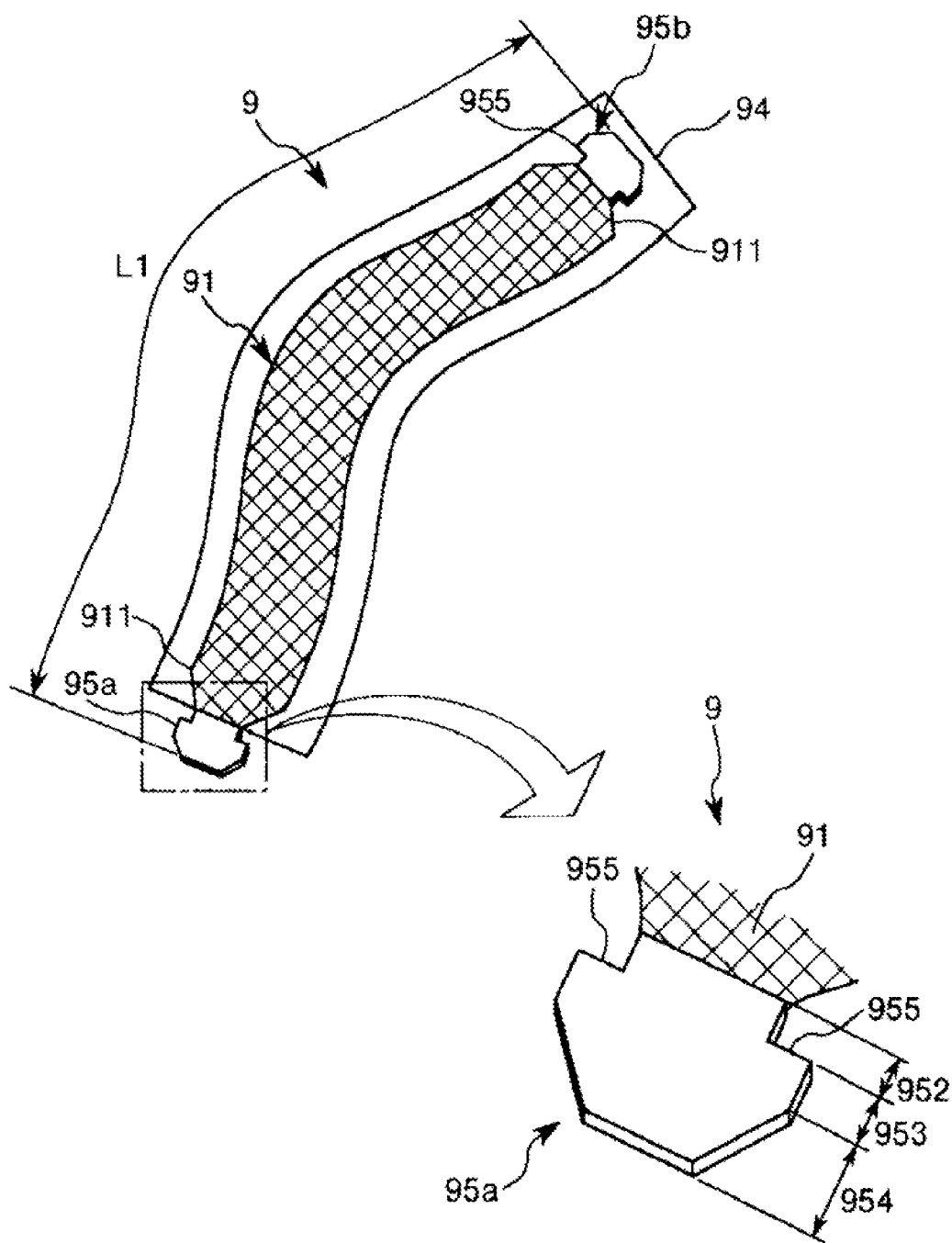
FIG. 10 is a perspective view showing an implant to be used in the method of placing an implant indwelling according to the first exemplary embodiment of the present disclosure.

As shown in FIG. 10, the implant 9 can include the implant main body 91, and anchor portions 95a and 95b provided respectively at both end portions of the implant main body 91. In accordance with an exemplary embodiment, the implant main body 91 and the anchor portion 95*b* can be accommodated in a wrapping material 94, which can help protect the implant 9.

Figure 19A:
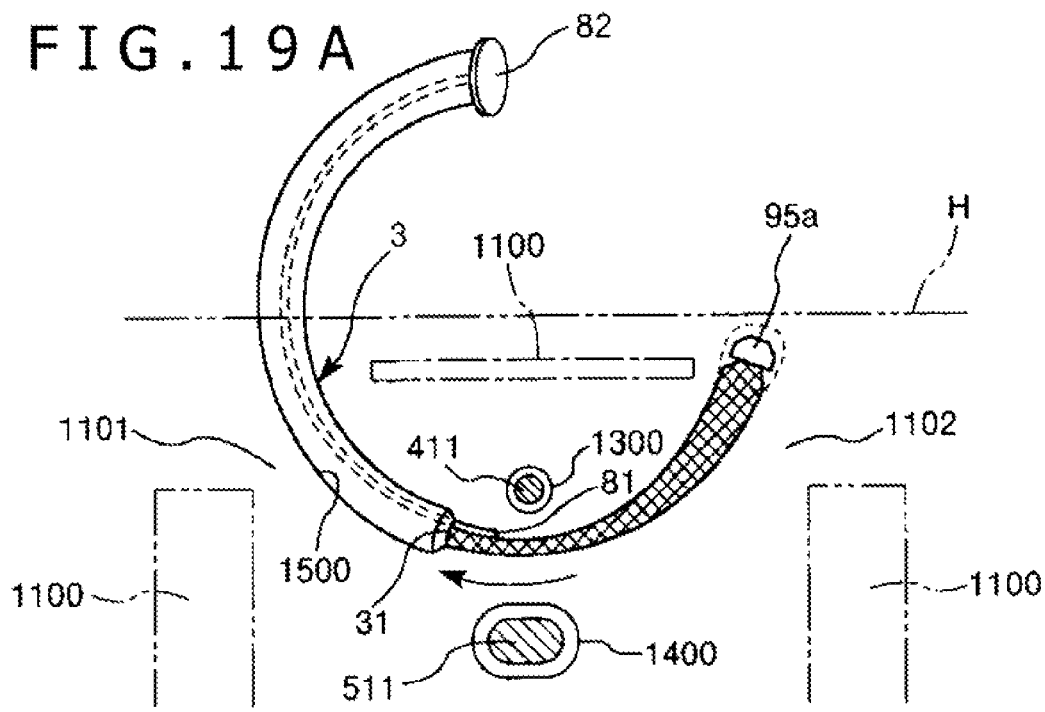
FIGS. 19A and 19B are views for illustrating the procedure of placing indwelling the implant shown in FIG. 10.
Figure 19B:
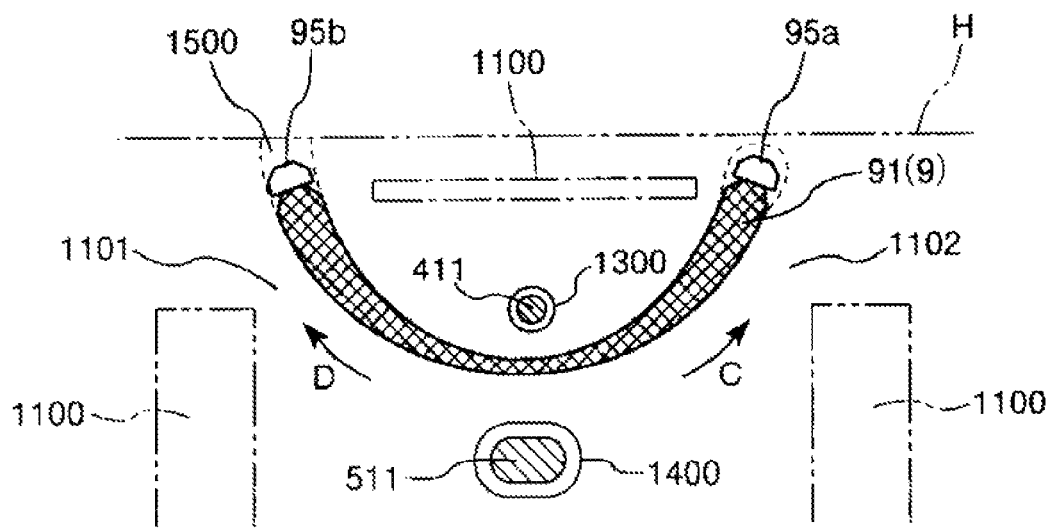

The implant main body 91 is a portion which is placed indwelling in a living body, and, in its indwelling state, supports the urethra 1300 (see FIG. 19B). The implant main body 91 can be composed essentially of a band body configured by use of a mesh (network body), and is lower in rigidity than the sheath 3. A length L1 of the implant main body 91 can be shorter than the length L2 of the sheath 3 (see FIGS. 4A and 10), which can help ensure that both ends of the implant main body 91 in the indwelling state are located at positions deviated in the depth direction from the body surface H, by a distance corresponding to the length by which the length L1 of the implant main body 91 is shorter than the length L2 of the sheath 3. Consequently, in the indwelling state, the implant main body 91 can avoid, neurons that are generally present in large numbers in the vicinity of the body surface H, which can help ensure that the patient is less liable to feel pain in the indwelling state of the implant main body 91. Accordingly, the burden on the patient can be relatively mitigated, even in the case where the implant main body 91 is left indwelling for a comparatively long period of time.

In addition, when a pressure is externally exerted on that part of the body surface H which corresponds to the implant main body 91 set indwelling, transmission of the pressure to the implant main body 91 can be moderated, since a biological tissue is present between the body surface H and the implant main body 91, which helps ensure that movement of the implant main body 91 in the inside of the living body can be restrained. As a result, a pain attendant on a movement of the implant main body 91 can be relatively suppressed.

In addition, at both end portions of the implant main body 91, there are formed decreasing-width portions 911 where the width of the implant main body 91 decreases, which helps ensure that formation of angular portions at the four corners of the implant main body 91 can be omitted. Therefore, for example at the time of inserting the implant main body 91 into the sheath 3, a part serving as a starting point for bending or folding can be omitted. Consequently, the implant main body 91 can assume a posture of being spread out, in the indwelling state.

In addition, a linear body constituting the implant main body 91 is not limited. Examples of the linear body applicable here include those, which can be circular in cross-sectional shape, and those which are flat-shaped in cross section.

The material constituting the implant main body 91 is not limited. Examples of the material applicable here include various biocompatible resin materials such as polypropylene, polyesters, nylon, etc. and fibers.

As shown in FIG. 10, the anchor portion 95*a* is provided on the lower side of the implant main body 91 in FIG. 10, and the anchor portion 95*b* is provided on the upper side of the implant main body 91 in FIG. 10.

The anchor portion 95*a* and the anchor portion 95*b* are the same in configuration, and, accordingly, the anchor portion 95*a* will be described below on a representative basis.

The anchor portion 95*a* can be a flat plate-like in shape, and is formed from a material higher in rigidity than a material constituting a network portion of the implant main body 91. The maximum width of the anchor portion 95*a* can be smaller than a width of the network portion of the implant main body 91, which can help ensure that, for example, at the time of inserting the implant main body 91 into the wrapping material 94, the anchor portion 95*a* can be prevented from obstructing the inserting operation.

In addition, the anchor portion 95*a* can be divided into a small width portion 952 interlocked to the network portion, a large width portion 953 greater than the small width portion 952 in width, and a decreasing-width portion 954 where the width decreases along a direction toward the side opposite to the network portion. The small width portion 952, the large width portion 953, and the deceasing-width portion 954 are provided in this order from the side of the network portion of the implant main body 91.

At a boundary portion between the small width portion 952 and the large width portion 953, there is formed a step portion 955 where the width of the anchor portion 95*a* can change abruptly, which helps permit the anchor portion 95*a* (step portion 955) to engage with a biological tissue in an indwelling state. As a result, the implant main body 91 is restricted in regard of movement in the directions of arrows C and D, for example, in the direction of arrow D, in FIG. 19B. In addition, by the anchor portion 95*b* provided on the side opposite to the anchor portion 95*a*, the implant main body 91 can be restricted in regard of movement in the directions of arrows C and D, for example, in the direction of arrow C, in FIG. 19B.

Thus, according to the anchor portion 95*a* and the anchor portion 95*b*, the implant main body 91 in the indwelling state can be restricted in regard of movement in the longitudinal direction of implant main body 91. Therefore, the indwelling state of the implant main body 91 can be maintained. Consequently, the implant main body 91 can support the urethra 1300 in a stable manner.

In accordance with an exemplary embodiment, the anchor portion 95*a* and the anchor portion 95*b* may each be configured to increase also in thickness along a direction toward the network portion of the implant main body 91. This, in conjunction with the engagement of the step portion 955 with a biological tissue, helps enable the indwelling state to be reliably maintained.

The material constituting the anchor portions 95*a* and 95*b* is not limited. Examples of the material applicable here include biocompatible resin materials.

The wrapping material 94 can be bag-like in shape, and can accommodate the implant main body 91 and the anchor portions 95*a* and 95*b*, which helps ensure that the implant main body 91 and the anchor portions 95*a* and 95*b* can be prevented from being contaminated.

Figure 17A:
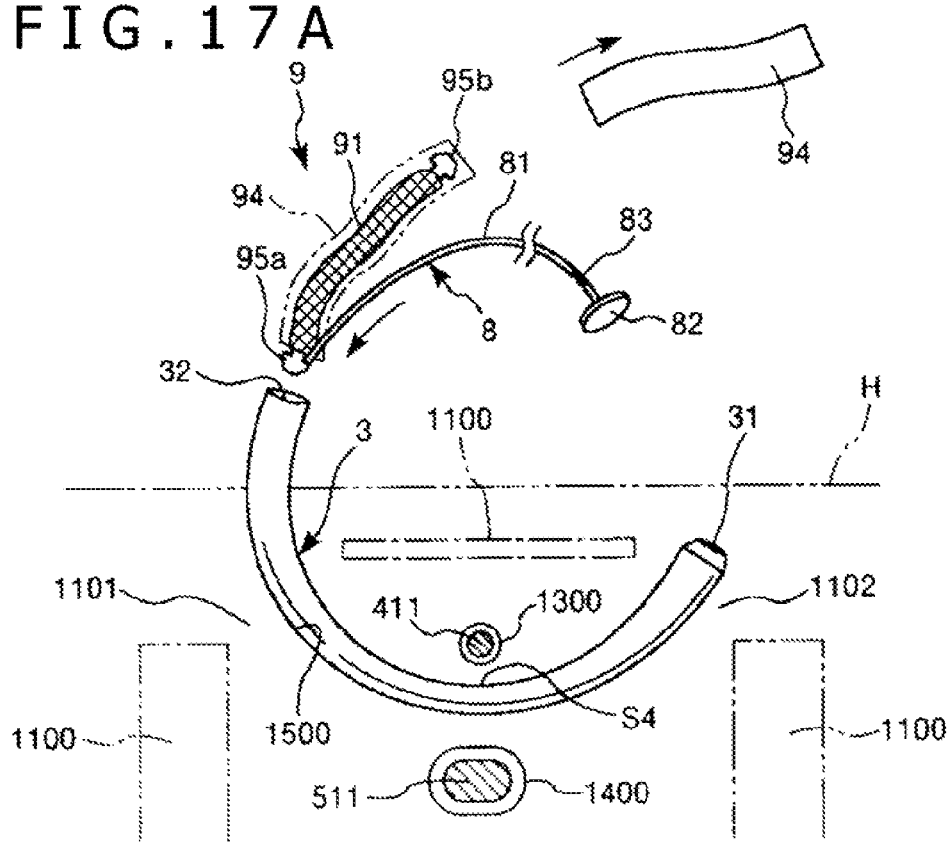
FIGS. 17A and 17B are views for illustrating a procedure of placing indwelling the implant shown in FIG. 10.
Figure 17B:
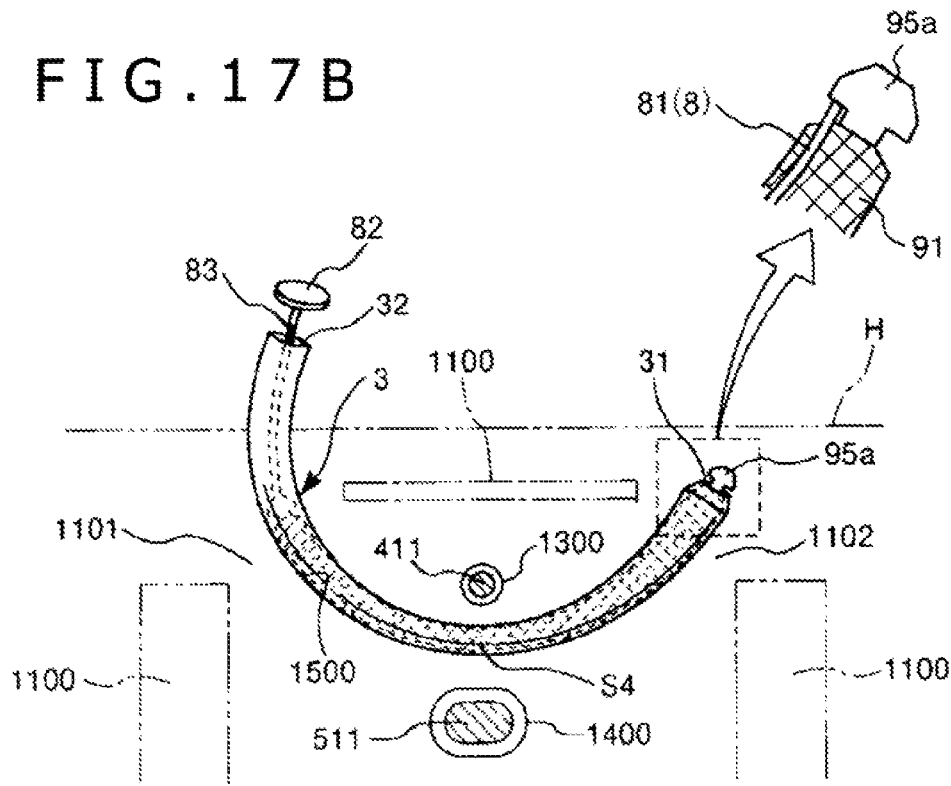

As shown in FIG. 17, the operating member 8 can include an operating member main body 81, a grasping portion 82 provided at a proximal portion of the operating member main body 81, and a marker 83 provided at an intermediate portion of the operating member main body 81 in the longitudinal direction. The operating member 8 can have a function of abutting on the anchor portion 95*a* and being operated to move the implant 9, at the time of inserting the implant 9 into the sheath 3 inserted in a living body.

The operating portion main body 81 can be elongated in shape, and can be curved along the curved shape of the sheath 3. A length of the operating portion main body 81 can be approximately equal to or slightly greater than the length of the sheath 3. In addition, an outside diameter of the operating member main body 81 can be constant, and can be smaller than an inside diameter of the sheath 3.

The grasping portion 82 is a portion to be grasped by an operator when the operator operates the operating member 8. The grasping portion 82 can be composed essentially of a flange, which can be enlarged in diameter, as compared with the outside diameter of the operating member main body 81.

In addition, the grasping portion 82 can function also as a restriction portion which restricts a limit of insertion of the operating member 8 into the sheath 3.

The marker 83 can be composed essentially of a colored portion, and has a function of indicating the position of the operating member 8 inside the sheath 3 (inside a living body). In this exemplary embodiment, the marker 83 is provided at such a position that a distance from a distal end of the operating member main body 81 to a position is approximately equal to the overall length of the sheath 3, which helps ensure that when the operating member 8 has been inserted into the sheath 3 and a distal end of the operating member 8 is protruding from a distal opening of the sheath 3 or is located at the same position as the distal opening, the position of a proximal end of the sheath 3 as spaced from the body surface H and the position of the marker 83 as spaced from the body surface H substantially coincide with each other.

Examples of the marker 83 include those formed by coating with a paint (coating film), printing, dyeing, sticking of a sticker, a weld (fused body) or the like. In addition, the color of the marker 83 is not limited. Examples of the color applicable here include various chromatic colors, achromatic colors, metallic colors, and fluorescent colors. The color of the marker 83 is necessary only to be different from the color of the operating member main body 81 (the surroundings of the marker 83).

According to the operating member 8 as disclosed above, the implant 9 can be easily inserted into the sheath 3.

In accordance with an exemplary embodiment, an operation procedure of the puncture apparatus 1 and a method of placing an implant indwelling according to the present disclosure will be described below.

Figure 11A:
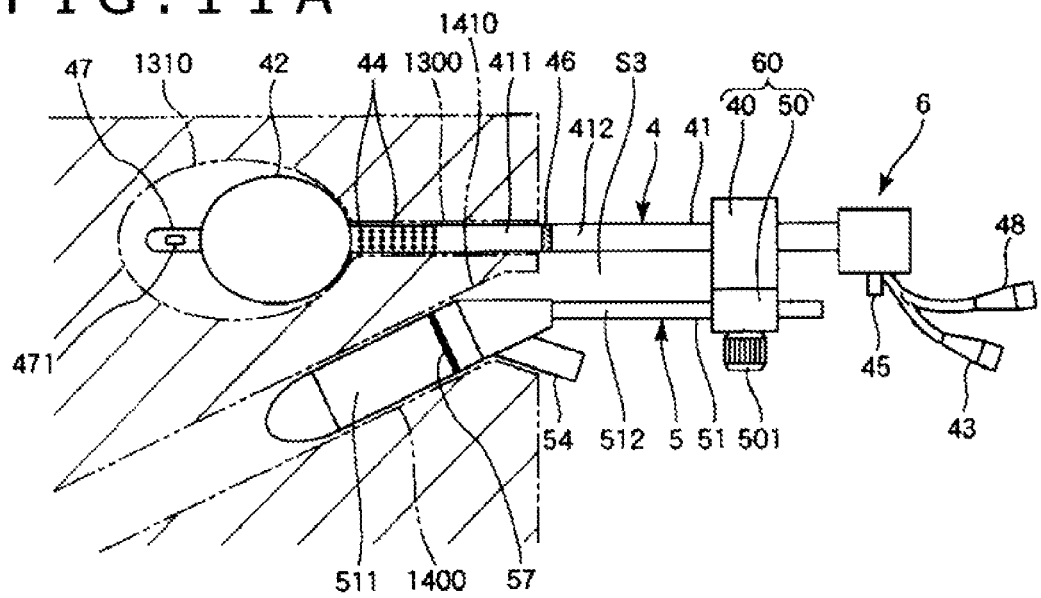
FIGS. 11A and 11B are views for illustrating an operation procedure of the puncture apparatus shown in FIG. 1.

First, a patient is put in a lithotomy position on an operating table, and the insertion instrument 6 is mounted onto the patient, as shown in FIG. 11A. For example, first, the urethral insertion portion 41 of the urethral insertion member 4 is inserted into the patient's urethra 1300. For example, while checking the depth of insertion by observing the marker 46, the balloon 42 is disposed inside the bladder 1310. The urethra 1300 is rectified into a predetermined shape by the urethral insertion portion 41 having the predetermined shape. In the case of this exemplary embodiment, the urethra can be rectified into a rectilinear shape by the urethral insertion portion 41 having the rectilinear shape.

Next, the balloon 42 is inflated, and, if necessary, urine is drained from the inside of the bladder 1310 through the drain hole 471. In addition, the vaginal insertion portion 51 of the vaginal insertion member 5 is inserted into the patient's vagina 1400. In this instance, while checking the puncture position by observing the marker 57, the vaginal insertion portion 51 is inserted to an appropriate depth. Then, the male screw 501 is operated, to fix the support portions 40 and 50. By this, mounting of the insertion instrument 6 onto the patient is completed. In this state, the non-insertion portions 412 and 512 are spaced from each other, the support part 60 is spaced from the body surface between the urethral orifice and the vaginal orifice, and that body surface is exposed. In addition, in the case where the insertion portion 511 and the anterior wall of vagina are spaced from each other and a gap (space) is formed therebetween, a space S3 for causing a syringe to puncture from the body surface between the urethral orifice and the vaginal orifice to a biological tissue between the urethra and the vagina, for example, to the anterior wall of the vagina, is formed.

Subsequently, suction devices are connected to the suction ports 45 and 54, and the suction devices are operated, whereby the urethra is sucked onto the urethral insertion portion 41, and the anterior wall of vagina is sucked onto the vaginal insertion portion 51. For example, when the urethra is properly sucked onto the urethral insertion portion 41, the suction holes 44 are closed with the urethral wall, so that the suction via the suction port 45 is stopped or weakened. Similarly, when the anterior wall of vagina is properly sucked onto the vaginal insertion portion 51, the suction holes 59 are closed with the vaginal wall, so that the suction via the suction port 54 is stopped or weakened. Therefore, based on the conditions of suction via the suction ports 45 and 54 (for example, a magnitude of sounds generated attendant on the suction via the suction ports 45 and 54), the operator can check whether or not the urethra and the anterior wall of vagina have been properly sucked onto the urethral insertion portion 41 and the vaginal insertion portion 51, respectively. It is to be noted that the insertion instrument 6 may be provided with a checking mechanism for mechanical checking of the sucked state. The checking mechanism is not limited, insofar as it enables checking of the sucked state. For example, the checking mechanism may be configured to include a flow measurement unit (negative-pressure sensor) for measuring a flow rate through the suction port 54 and a decision unit for deciding whether or not the sucking is being properly done, based on the measurement results sent from the flow measurement unit.

Figure 11B:
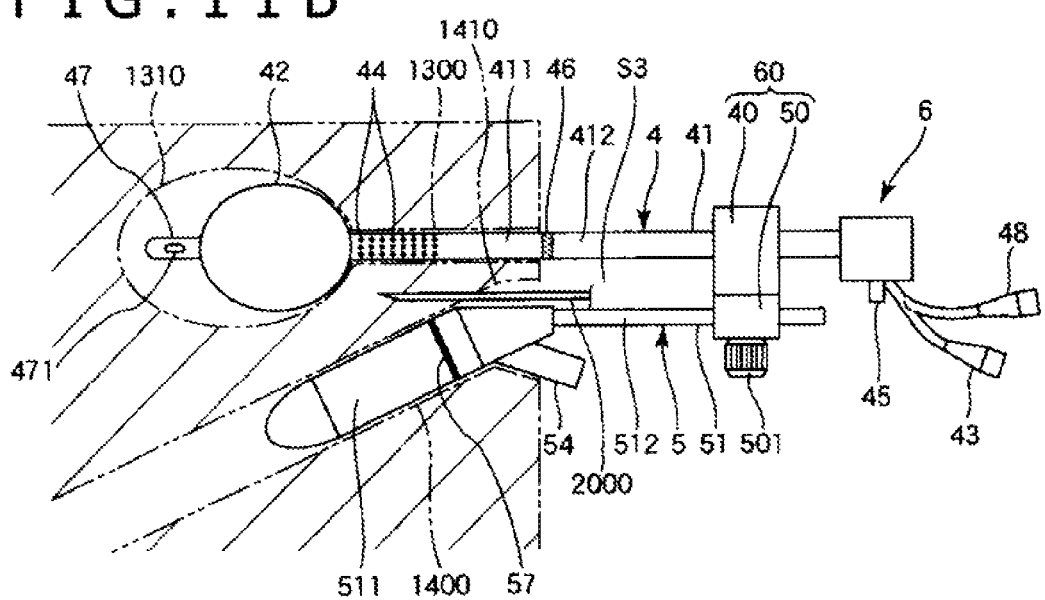

Next, humoral dissection is performed. For example, as shown in FIG. 11B, a puncture needle of a syringe 2000 is caused to puncture the anterior wall of vagina, 1410, by way of the space (space S3) between the insertion portion 511 and the anterior wall of vagina, 1410, and a liquid such as physiological salt solution or local anesthetic is injected into the biological tissue between the urethra 1300 and the vagina 1400 (between the regions S1 and S2). As a result, the biological tissue between the regions S1 and S2 is expanded, the urethra is pressed against the urethral insertion portion 41, and the anterior wall of vagina, 1410, is pressed against the vaginal insertion portion 51.

Here, it can be preferable that the suction through the suction holes 44 and 59 is continuously conducted also during the humoral dissection. When the urethra is pressed against the urethral insertion portion 41 due to the humoral dissection, the urethra is further sucked onto the urethral insertion portion 41, so that the suction via the suction port 45 is stopped or weakened. Similarly, when the anterior wall of vagina is pressed against the vaginal insertion portion 51, the anterior wall of vagina is further sucked onto the vaginal insertion portion 51, so that the suction via the suction port 54 is stopped or weakened. Based on the conditions of suction via the suction ports 45 and 54, therefore, the operator can check whether or not the humoral dissection has been properly performed.

Figure 12A:
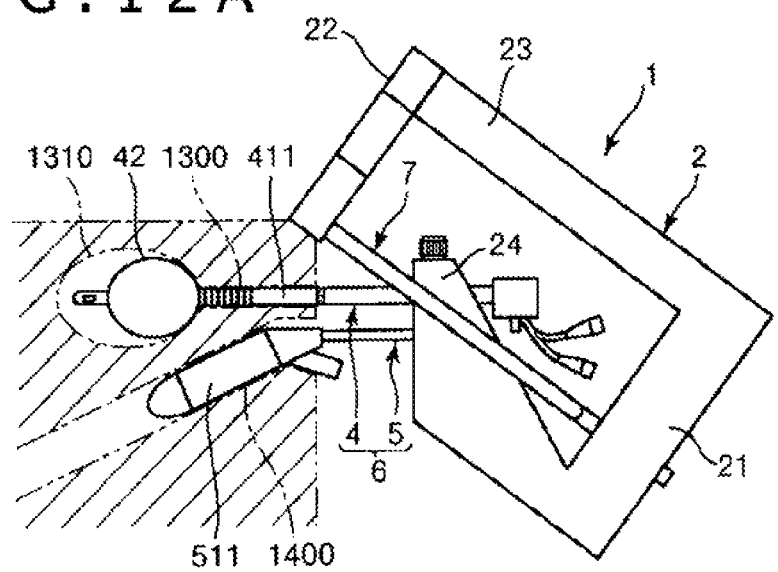
FIGS. 12A and 12B are views for illustrating the operation procedure of the puncture apparatus shown in FIG. 1.
Figure 13:
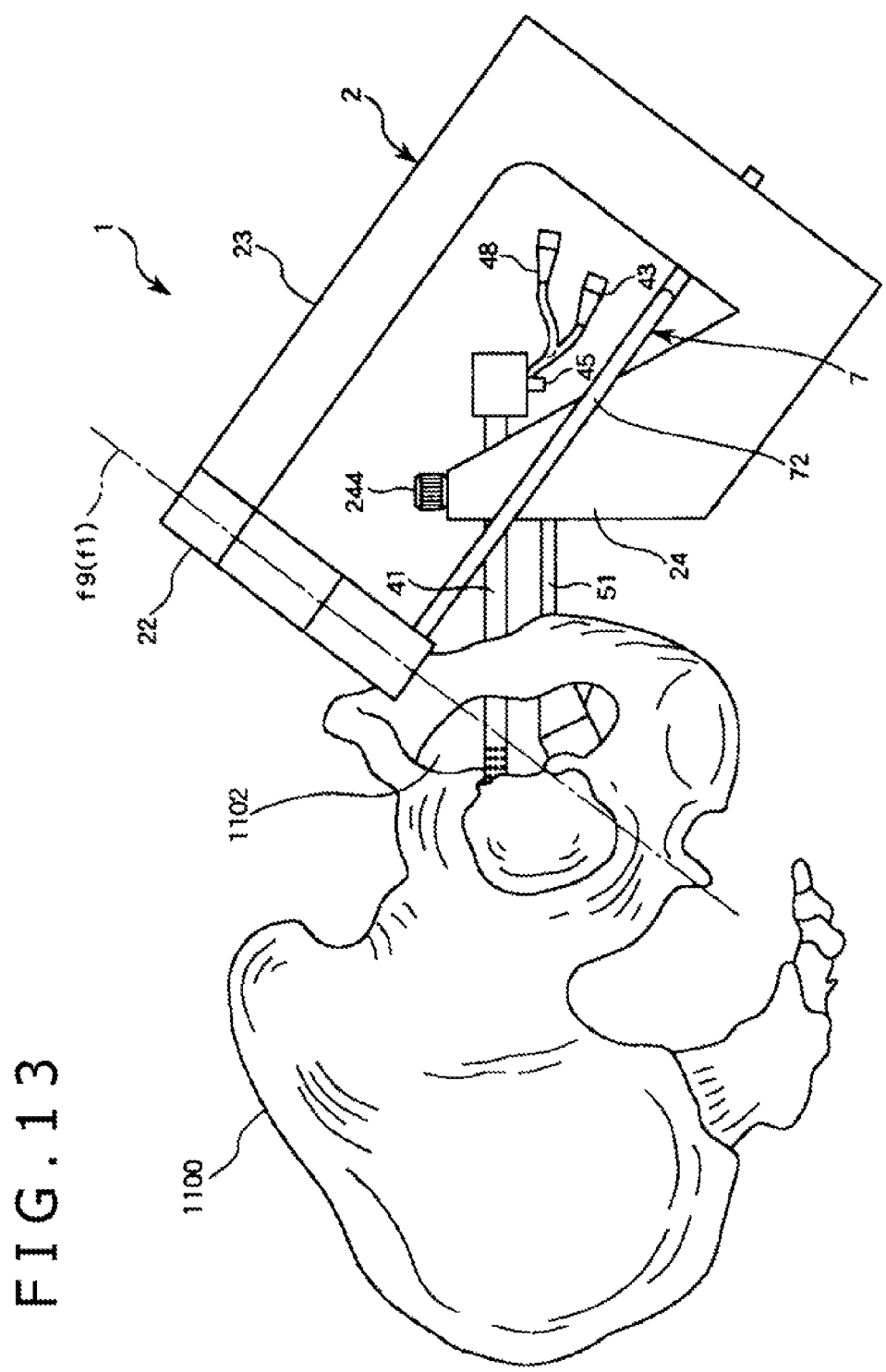
FIG. 13 is a side view illustrating the relationship between the puncture apparatus and the pelvis in the state shown in FIG. 12A.

After the humoral dissection is conducted so that the urethra and the anterior wall of vagina are thereby sufficiently spaced from each other, the frame 2 is fixed to the insertion instrument 6, as shown in FIG. 12A. This results in that the puncture apparatus 1 is mounted on the patient. In this state, a positional relationship between the pelvis 1100 and the puncture apparatus 1 is as shown in FIG. 13.

Figure 12B:
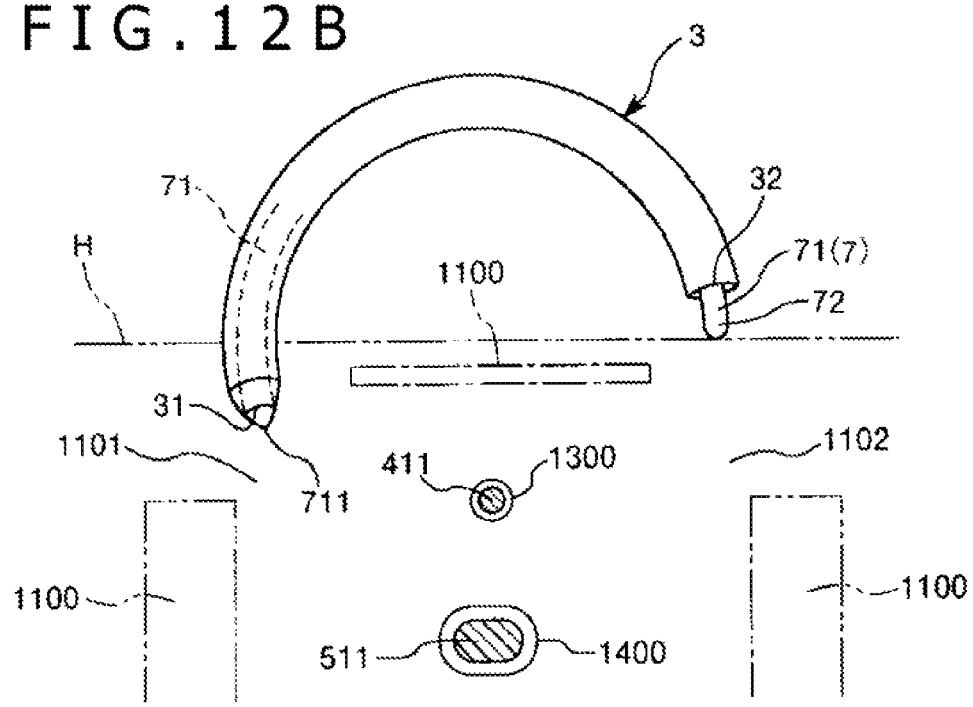

Next, for example, while grasping the interlock portion 23 of the frame 2 by one hand, the interlock portion 72 of the puncture member 7 is grasped by the other hand, and the puncture member 7 is rotated counterclockwise, as shown in FIG. 12B. In this instance, the needle tip 711 punctures a body surface H at a patient's right-hand inguinal region or a region in the vicinity thereof (first region) to enter the body, and sequentially passes the obturator foramen 1101 on one side, a region between the urethra 1300 and the vagina 1400, and the obturator foramen 1102 on the other side, when the turning operation is stopped (see FIG. 14A).

Figure 15:
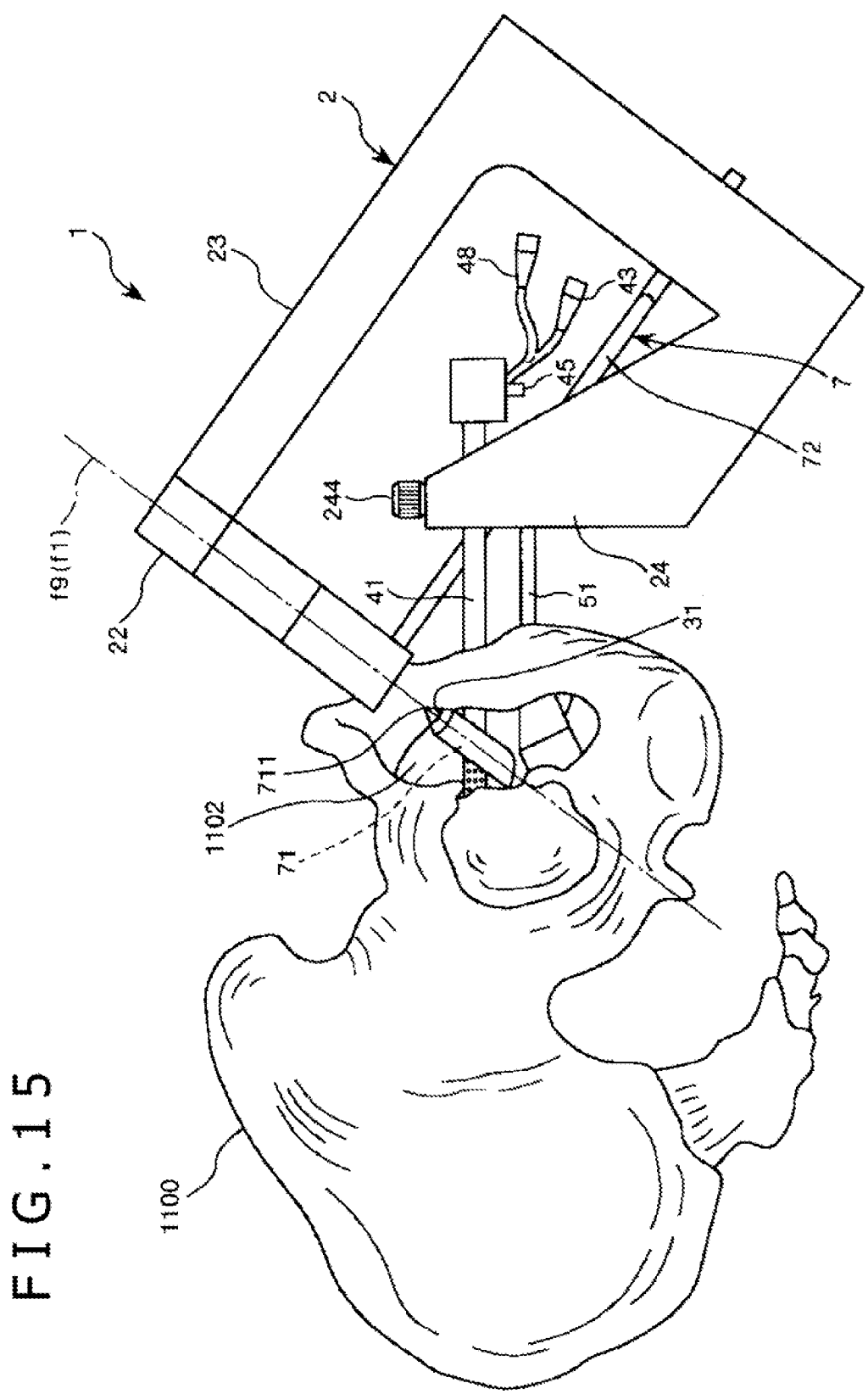
FIG. 15 is a side view illustrating the positional relationship between the puncture apparatus and pelvis in the state shown in FIG. 14A.

As a result, an insertion hole 1500 is formed, which has its one end opening in the body surface H, has its other end closed in relation to the body surface H, and which is passing between the urethra 1300 and the vagina 1400. In this state, the positional relationship between the pelvis 1100 and the puncture apparatus 1 is as shown in FIG. 15.

Figure 14A:
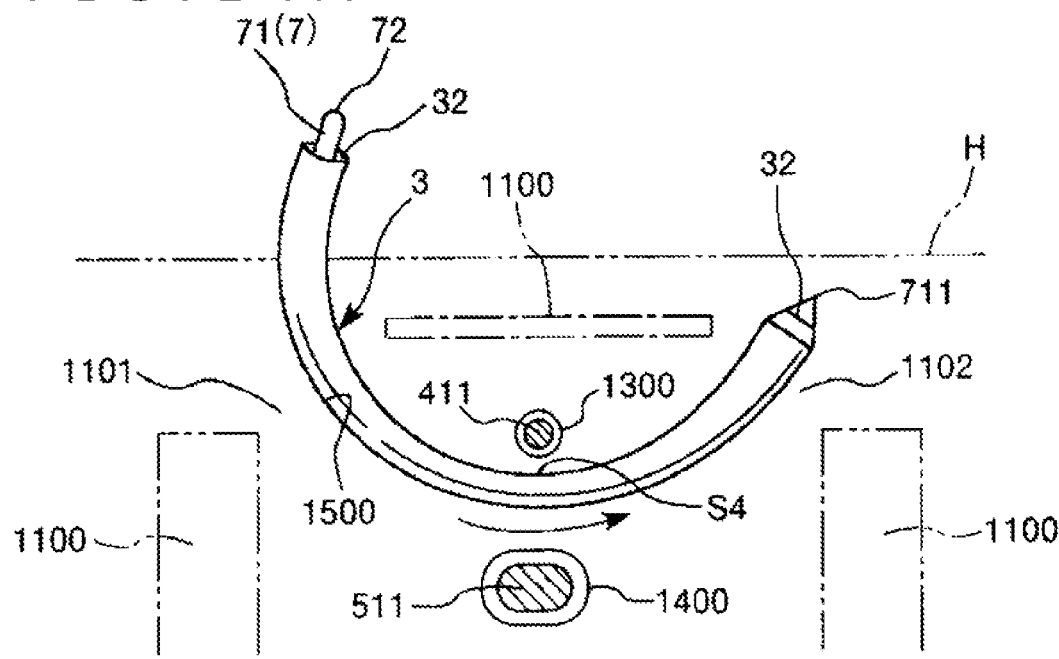
FIGS. 14A and 14B are views for illustrating the operation procedure of the puncture apparatus shown in FIG. 1.
Figure 14B:
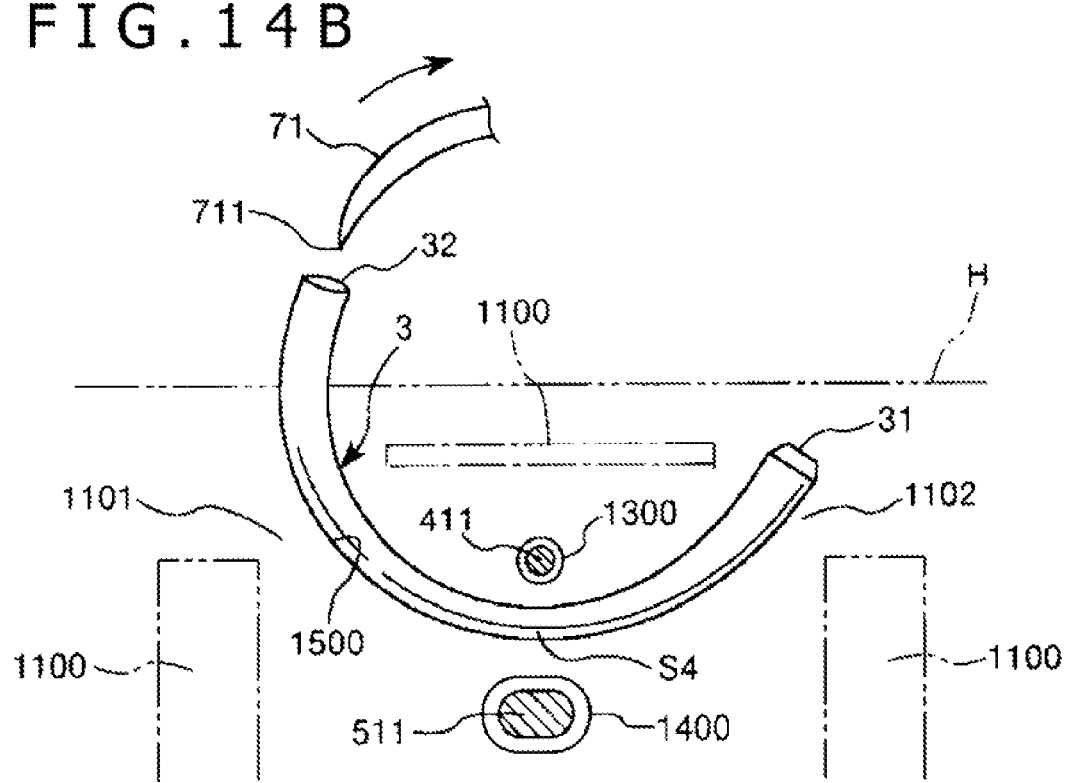

Subsequently, the puncture member 7 is rotated clockwise in FIG. 14B. In this instance, for example while holding down the sheath 3 by fingers on one side, the puncture member 7 is pulled out so that the sheath 3 is left indwelling in the living body. By this, only the puncture member 7 is pulled out of the living body. In addition, in this state, a proximal portion of the sheath 3 can protrude from the body surface H to the outside.

In the state shown in FIG. 16, the sheath 3 can be disposed so that its width direction (the direction of the major axis J32) W is substantially parallel to the urethra 1300. For example, the urethra 1300 rectified by the insertion of the urethral insertion member 4 into the urethra 1300 and the width direction of the sheath 3 can be practically parallel to each other.

Next, as shown in FIG. 17A, while taking the implant 9 out of the wrapping material 94, the implant 9 is inserted into the proximal end opening 32 of the sheath 3, starting from the anchor portion 95a side. In this instance, while grasping the grasping portion 82 of the operating member 8, a distal portion of the operating portion main body 81 is put in abutment on the anchor portion 95a (step portion 95b), and is operated to move the implant 9 forward in the inserting direction. By this, the implant 9 can be easily inserted into the sheath 3. In addition, since the operating member main body 81 is curved along the curved shape of the sheath 3, a simple operation of pushing in the operating member main body 81 toward the living body side causes the operating member main body 81 to be guided by the sheath 3, whereby the implant 9 can be moved within the sheath 3. This moving operation is performed until the anchor portion 95a is exposed via the distal end opening 31 of the sheath 3.

Furthermore, the operating member 8 is provided with the marker 83, as aforementioned. An adjustment is conducted so that the marker 83 and the proximal end of the sheath 3 will be equidistant from the body surface H. For example, the operating member 8 can be inserted into the sheath 3 until the marker 83 and the proximal end of the sheath 3 become equidistant from the body surface H. As a result, the distal end of the operating member main body 81 and the distal end of the sheath 3 are substantially the same in depth of insertion into the living body. Therefore, this results in that the position of the anchor portion 95a in abutment on the operating member main body 81 and the position of the distal end opening 31 of the sheath 3 are substantially the same, and the anchor portion 95a is exposed from the distal end opening 31. In this state, a central portion of the implant main body 91 is located between the urethra 1300 and the vagina 1400 (see FIG. 18).

In this way, the anchor portion 95a (step portion 95b) can function also as an abutment portion which abuts on the operating member 8 and which is operated by the operating member 8.

Figure 18:
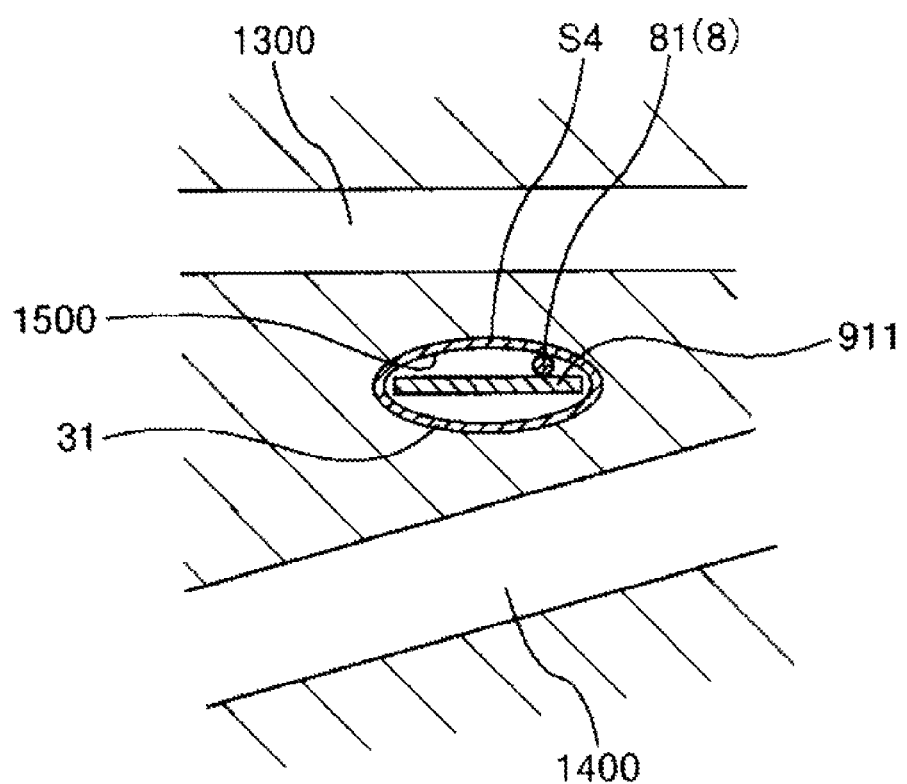
FIG. 18 is a sectional view illustrating the posture of the puncture member relative to the urethra in the state shown in FIG. 17B.

In accordance with an exemplary embodiment, since the sheath 3 is flat-shaped as aforementioned, the posture of the implant main body 91 in the inserted state follows the flat shape. For example, the implant main body 91 can be disposed in the sheath 3 in such a manner that its width direction coincides with the width direction of the sheath 3, as shown in FIG. 18, which helps ensure that the implant main body 91 is disposed in parallel to the urethra 1300, which is in the rectified form.

Next, the sucking of the urethra by the urethral insertion portion 41 and the sucking of the anterior wall of vagina, 1410, by the vaginal insertion portion 51 are stopped. As a result, the positions and shapes of the urethra 1300 and the vagina 1400 are returned into the original positions and shapes in the natural state.

Subsequently, as shown in FIG. 19A, a proximal portion of the sheath 3, for example, that portion of the sheath 3 which is exposed to the outside of the living body, is grasped by fingers or the like, and the sheath 3 is pulled out proximally. In this instance, the surrounding tissue having been forced spread or expanded by the sheath 3 returns into its original position, and the tissue comes into contact with the implant main body 91 gradually from the distal end toward the proximal end.

In accordance with an exemplary embodiment, when the sheath 3 is pulled out proximally, a proximal portion of the sheath 3 abuts on the grasping portion 82 of the operating member 8. By a simple operation of grasping the sheath 3 and pulling it out, therefore, the operating member 8 can also be pulled out of the living body, together with the sheath 3.

In addition, the sheath 3 has an internal space in which the implant main body 91 can be moved under a sufficiently low sliding, which helps ensure that the implant main body 91 can be placed indwelling in an as-is state, with no unnecessary tensile force exerted thereon. Accordingly, there is no need for control of tension on the implant main body 91. As a result of these operating steps, the implant 9 is in the state of being set indwelling in the living body, as shown in FIG. 21B.

In accordance with an exemplary embodiment, since the implant 9 is provided with the anchor portions 95a and 95b, the implant 9 can be restricted in regard of movement in the longitudinal direction of the insertion hole 1500 by the anchor portion 95a, which can help ensure that the indwelling state of the implant 9 can be reliably maintained.

In addition, since the sheath 3 is pulled out of the living body in the state in which the urethral insertion member 4 is inserted in the urethra 1300, excessive tension from being exerted on the urethra 1300 by the implant main body 91 which is placed indwelling in the living body can be relatively prevented.

Next, the urethral insertion member 4 is pulled out of the urethra 1300, and the vaginal insertion member 5 is pulled out of the vagina 1400. After the urethral insertion member 4 is pulled out, the urethra 1300 returns into its shape in the natural state. In this case, since the implant main body 91 is embedded in the biological tissue, the state in which the urethra 1300 in the natural state and the implant main body 91 are parallel to each other can be maintained.

In addition, in this indwelling state, the implant 9 is in the indwelling state, and is located deep from the body surface H, which helps ensure that burden on the patient can be alleviated, even in the case where the implant 9 is left indwelling for a comparatively long period of time.

In addition, the use of the puncture apparatus 1 can help ensure that the operation for placing the implant indwelling can be dealt with only a less invasive procedure such as puncture by the sheath 3, without need to perform a heavily invasive incision or the like. Therefore, relatively less burdensome on the patient and relative high safety for the patient can be obtained. In addition, since the implant main body 91 can be implanted in parallel to the urethra 1300, the urethra 1300 can be supported in a wider region. In addition, the living body can be punctured by the sheath 3 while avoiding the urethra 1300 and the vagina 1400, so that the sheath 3 can be prevented from puncturing the urethra 1300 or the vagina 1400; thus, safety is secured. In addition, the issues encountered in the case of conventional incision of vagina, such as an issue that the implant 9 would be exposed to the inside of the vagina via a wound formed by the incision, or an issue of complications due to infection via the wound can be prevented. Thus, the operation with the puncture apparatus 1 is relatively safe, and the implant 9 can be reliably implanted.

Furthermore, at the time of puncturing a living body by the puncture apparatus 1, the rotating operation is stopped when the needle tip 711 having entered the living body from the body surface H has passed the obturator foramens 1101 and 1102, whereby an insertion hole 1500 is formed which has its one end opening in the body surface H and its other end not opening in the body surface H. The implant is inserted into the insertion hole 1500, whereby the number of openings of wound formed in the body surface H can be minimized. Consequently, the implant 9 can be inserted in the living body with a very low invasiveness.

In the method of placing an implant indwelling according to the present disclosure, the sheath 3 is introduced into the living body prior to placing of the implant 9 indwelling in the insertion hole 1500, whether or not the implant 9 can be disposed in a suitable position in the living body can be checked. If the sheath 3 has been introduced to an unsuitable position in the living body, the sheath 3 can be pulled out of the living body, and the sheath 3 can be re-inserted into a suitable position in the living body.

FIGS. 20 and 21 are views for illustrating a procedure of a method of placing an implant indwelling according to a second exemplary embodiment of the present disclosure. Referring to these figures, the second exemplary embodiment of the method of placing an implant indwelling according to the present disclosure will be described below. The following description will center on differences from the above-described exemplary embodiment, and descriptions of the same items as those mentioned above will be omitted.

This exemplary embodiment is substantially the same as the first exemplary embodiment above, except for a difference in the procedure of placing an implant indwelling.

Figure 20A:
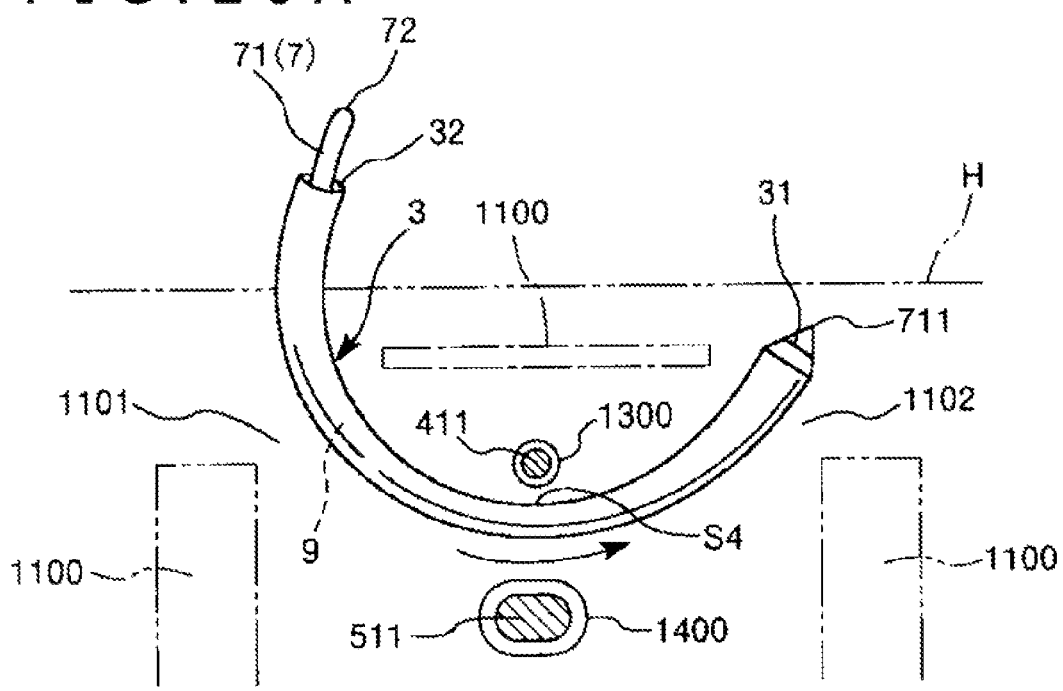
FIGS. 20A and 20B are views for illustrating a procedure of a method of placing an implant indwelling according to a second exemplary embodiment of the present disclosure.
Figure 20B:
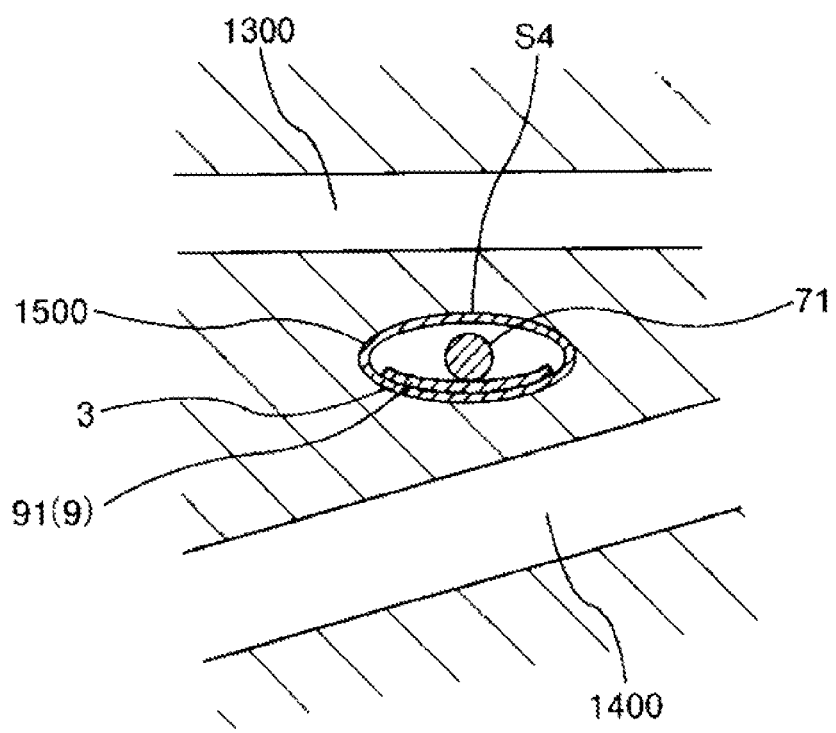

As shown in FIGS. 20A and 20B, in a state in which a puncture member 7 is inserted in a sheath 3, an implant 9 is preliminarily inserted between a puncture portion 71 and the sheath 3. In addition, an overall length of an operating member 8A is larger than the overall length of the operating member 8 in the first exemplary embodiment.

In use of a puncture apparatus 1 as above, when the puncture member 7 is pulled out of the sheath 3 after formation of an insertion hole 1500 by a turning operation, as shown in FIG. 20A, the implant 9 is present inserted in the sheath 3 left indwelling in the living body.

Figure 21A:
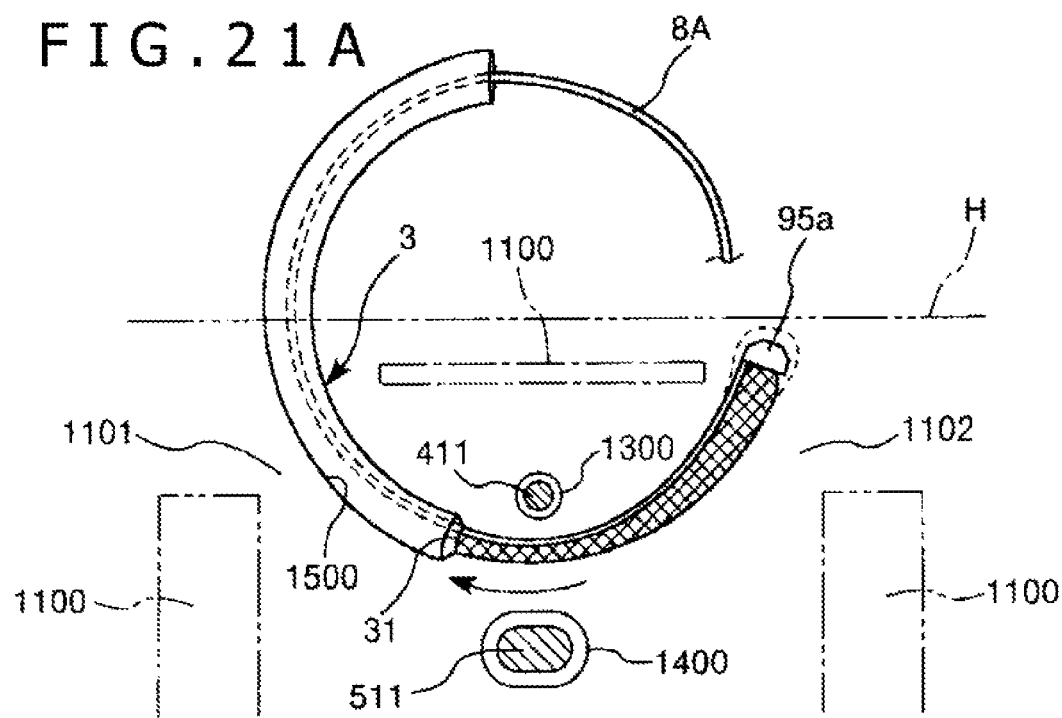
FIGS. 21A and 21B are views for illustrating the procedure of the method of placing the implant indwelling according to the second exemplary embodiment of the present disclosure.
Figure 21B:
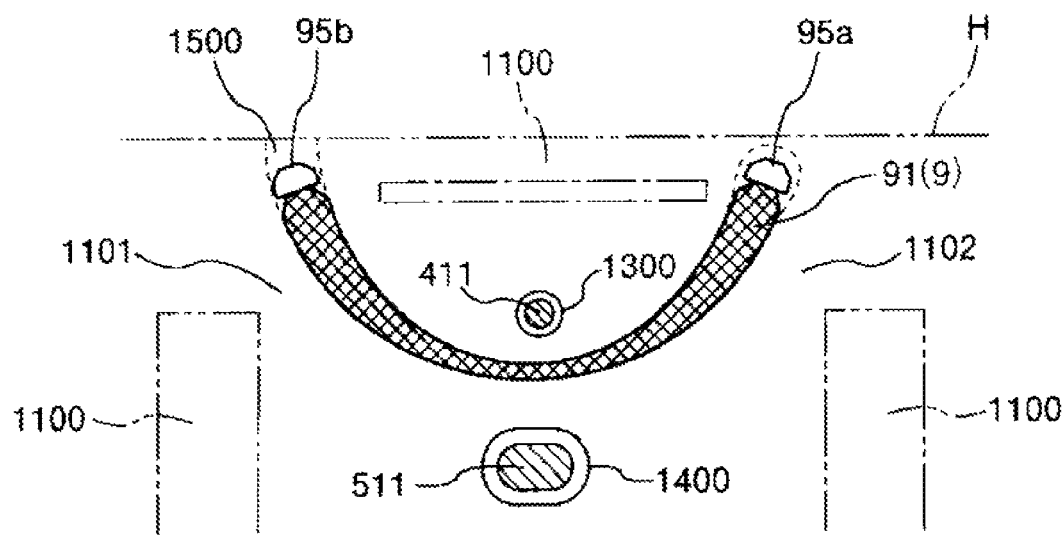

In this state, the sheath 3 is pulled out of the living body so that the implant 9 will be placed indwelling in the living body (see FIG. 21A). In this instance, the operating member 8A is inserted into the sheath 3 via a proximal end opening 32 of the sheath 3, and is put into abutment on an anchor portion 95a. In this abutted state, the sheath 3 is pulled proximally, while maintaining a depth of insertion of the operating member 8A. When the sheath 3 is moved proximally, the implant 9 may tend to move proximally together with the sheath 3. However, a distal end of the operating member 8A is in abutment on the anchor portion 95a and, hence, is maintaining a depth of insertion of the anchor portion 95a. Therefore, the implant 9 can be securely prevented from moving proximally together with the sheath 3. Consequently, the implant 9 is placed indwelling in the living body in a reliable manner.

Then, when the anchor portion 95a has just been exposed from a distal end opening 31 of the sheath 3, the restriction of the implant 9 by the operating member 8A is stopped. For example, when the anchor portion 95a has just been exposed from the distal end opening 31 of the sheath 3, the operating member 8A is pulled out together with the sheath 3. In this instance, the anchor portion 95a is caught on the biological tissue, so that the anchor portion 95a is prevented from moving proximally together with the sheath 3.

In accordance with an exemplary embodiment, movement of the implant 9 may be restricted by the operating member 8A continuously until the sheath 3 has been pulled out of the living body. In this case, the operating member 8A has such a length that the sheath 3, with the operating member 8A inserted and passed in the sheath 3, can be moved a distance corresponding to its overall length (L2).

In addition, the operating member 8A may be elastic to such an extent as to be able to push the anchor portion 95a, which helps ensure that, while the operating member 8A is sufficiently long and a proximal end of the operating member 8A may accordingly tend to make contact with a body surface H, such a contact can be avoided by elastically deforming the operating member 8A.

In addition, in the case where the operating member 8A is sufficiently long and at least its portion to be inserted in the sheath 3 is comparable in rigidity to the sheath 3, the sheath 3 can be pulled out of the living body smoothly and easily. In this case, further, unnecessary force from being exerted on the implant 9 at the time of pulling the sheath 3 out of the living body can be prevented.

As above-described, according to the method of placing the implant indwelling in this exemplary embodiment, the implant 9 and the sheath 3 are inserted together into a living body, and, therefore, an operation of inserting the implant 9 into the sheath 3 having been inserted in the living body can be omitted. Accordingly, the implant 9 can be placed indwelling, relatively swiftly and easily. As a result, the implant 9 can be placed indwelling with a further lowered invasiveness.

Figure 22:
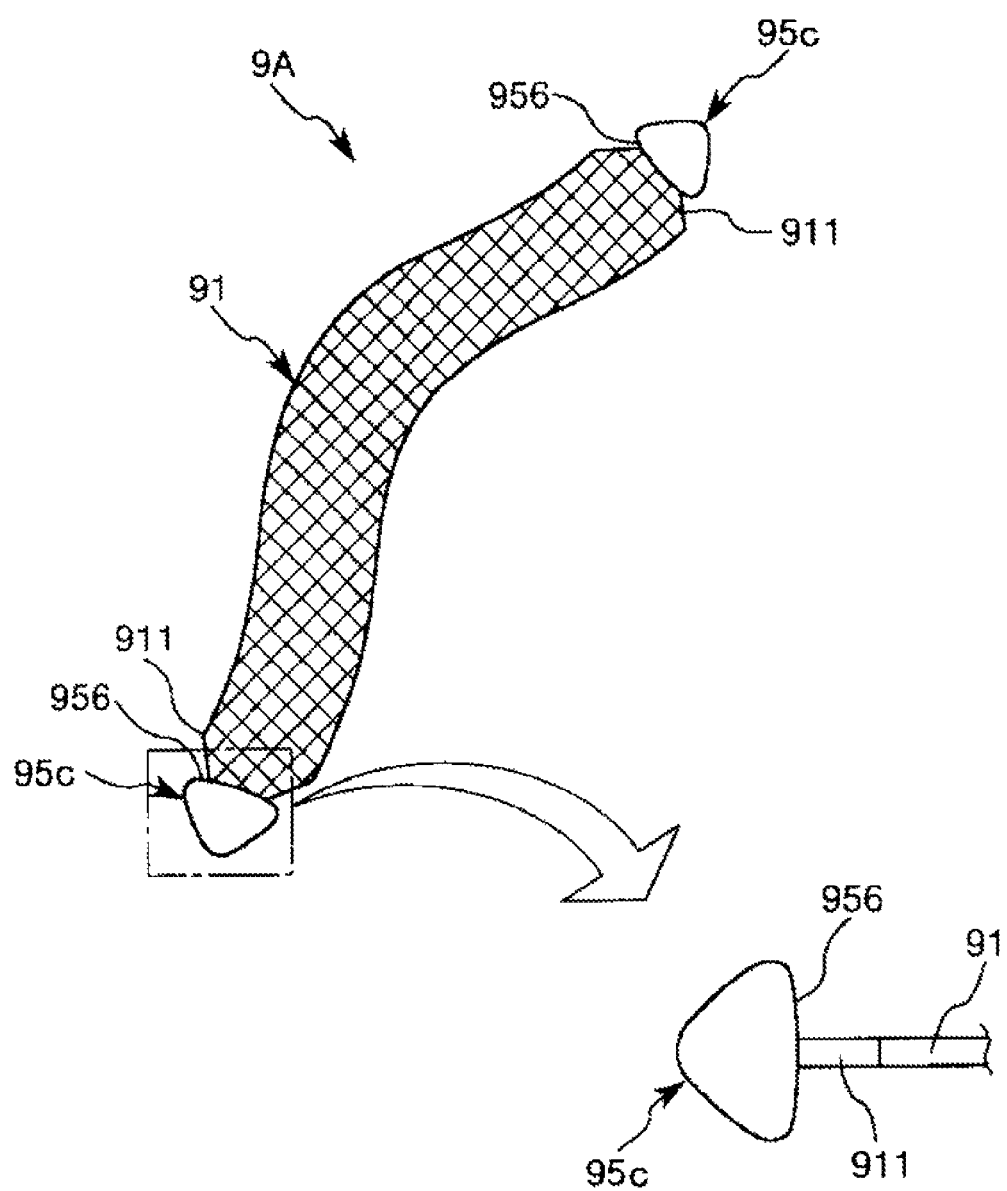
FIG. 22 is a perspective view showing an implant to be used in a method of placing an implant indwelling according to a third exemplary embodiment of the present disclosure.

FIG. 22 is a perspective view showing an implant to be used in a method of placing an implant indwelling according to a third exemplary embodiment of the present disclosure.

Now, referring to this figure, the third exemplary embodiment of the method of placing an implant indwelling according to the present disclosure will be described below. The following description will center on differences from the above-described exemplary embodiments, and descriptions of the same items as those mentioned above will be omitted.

This exemplary embodiment is the same as the first exemplary embodiment above, except for a difference in the configuration (shape) of the implant.

As shown in FIG. 22, in an implant 9A, each of anchor portions 95c can be rounded-apexed cone-like in shape. A base surface 956 of the anchor portion 95c is a flat surface which is circulate in plan view, which helps ensure that at the time of putting an operating member 8 in abutment on the anchor portion 95c, the circular shape of the base surface 956, or the spreading of the anchor portion 95c in the direction of circumference, permits a distal portion of the operating member 8 to come into abutment on the anchor portion 95c. Furthermore, at the time of operating the operating member 8 for movement, the operation can be reliably carried out.

Figure 23:
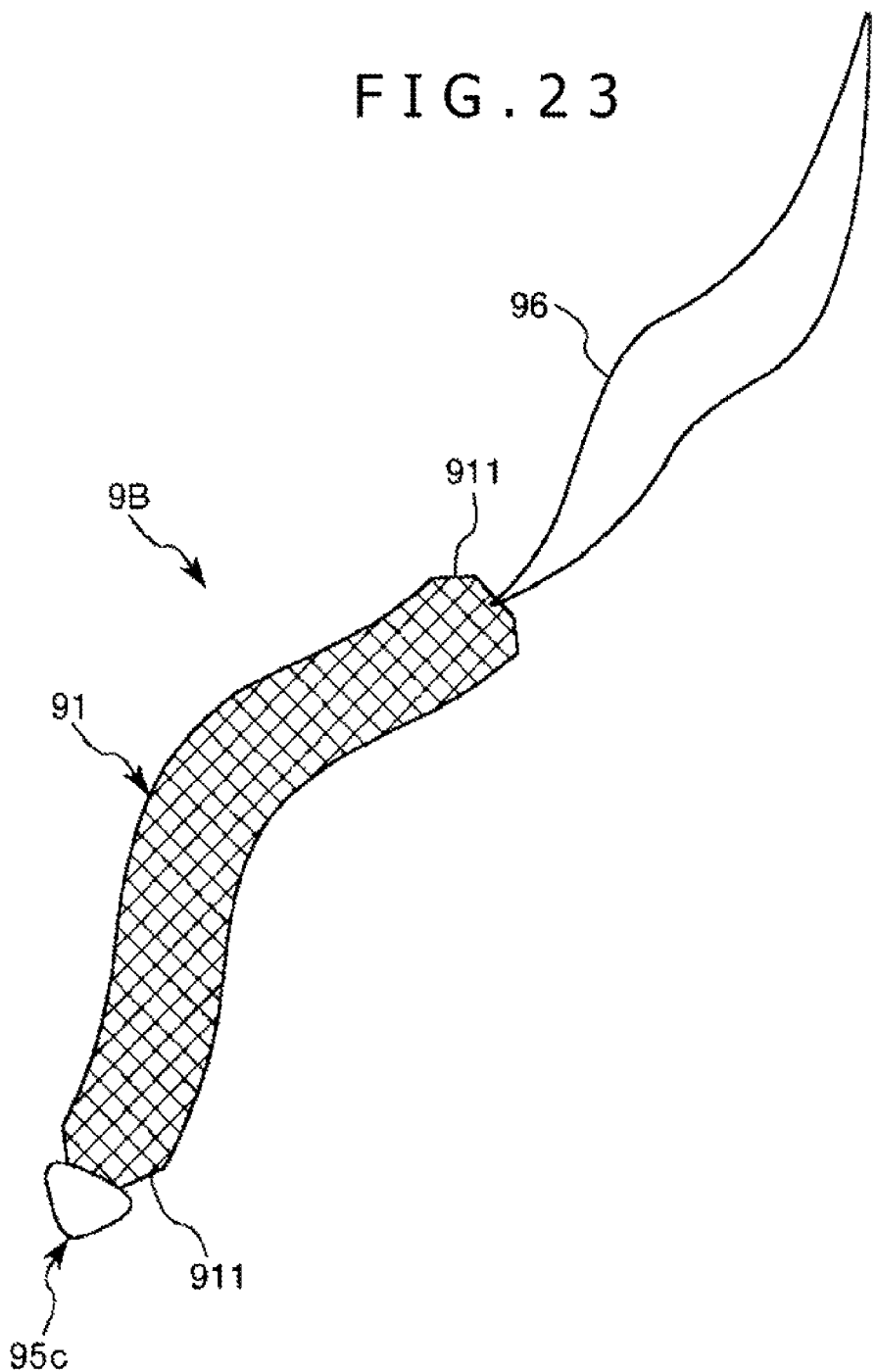
FIG. 23 is a perspective view showing an implant to be used in a method of placing an implant indwelling according to a fourth exemplary embodiment of the present disclosure.

FIG. 23 is a perspective view showing an implant to be used in a method of placing an implant indwelling according to a fourth exemplary embodiment of the present disclosure.

Now, referring to this figure, the fourth exemplary embodiment of the method of placing an implant indwelling according to the present disclosure will be described below. The following description will center on differences from the above-described exemplary embodiments, and descriptions of the same items as those mentioned above will be omitted.

This exemplary embodiment is the same as the third exemplary embodiment, except for a difference in the configuration (shape) of the implant.

As shown in FIG. 23, in an implant 9B, one of the anchor portions 95c in the third exemplary embodiment above is omitted. In this case, at the time of inserting the implant 9B into a sheath 3 having been placed indwelling in a living body, the implant 9B is inserted starting from the anchor portion 95c side.

This implant 9B helps ensure that at the time of pulling out an operating member 8 after the implant 9B is placed indwelling, the implant 9B can be prevented from obstructing the operation of pulling out the operating member 8, since the anchor portion 95c on a proximal end has been omitted. Therefore, the operation of pulling out the operating member 8 can be carried out smoothly.

In addition, a loop-formed string 96 is interlocked to an end portion, on the side opposite to the anchor portion 95c, of an implant main body 91. The string 96 preferably has such a length as to protrude from a proximal end opening 32 of the sheath 3 when the implant main body 91 is inserted and placed indwelling in the sheath 3 that has been placed indwelling in a living body, which helps ensure that in the indwelling state, part of the loop-formed string 96 is exposed to the outside of the living body. With the anchor portion 95c fixed by the operating member 8, the exposed part of the string 96 is pulled, whereby control of tension on the implant main body 91 can be performed.

In addition, by cutting the exposed part of the string 96, the string 96 can be pulled out easily.

While the method of placing the implant indwelling according to the present disclosure has been described above referring to the exemplary embodiments illustrated in the drawings, the disclosure is not restricted to the above exemplary embodiments. Each of the components can be replaced by a component having such a configuration as to have an equivalent function. In addition, an arbitrary structure or structures may be added to the original structures according to the present disclosure.

It is to be noted that while a procedure in which a turning operation in puncturing a living body is stopped in its course so that a needle tip does not pierce (pass through) the living body is adopted in the aforementioned exemplary embodiments, this is not restrictive of the present disclosure. Instead, a puncture portion may be provided with a stopper or the like, thereby restricting a limit of insertion of the puncture portion into the living body. In addition, the puncture portion may be provided at its distal end with a comparatively non-sharp, or "blunt," needle tip. In that case, that part of the body surface which will be passed by the puncture portion is cut, the puncture portion is inserted via the cut part, and a turning operation is conducted. Even if this turning operation is performed excessively, the "blunt" needle tip would not pierce (pass through) the body surface. Consequently, an insertion hole having one end closed in relation to the body surface can be reliably formed.

It is to be noted that in the case where each anchor portion of the implant is omitted, the implant main body is directly operated by the operating member, at the time of inserting the implant into the sheath that has been placed indwelling in a living body. In such a situation, the operating member is preferably provided at its distal portion with a hook portion on which a network portion of the implant main body is to be hooked for the purpose of operating. Such a hook portion is not specifically limited. Examples of the hook portion applicable here include a bifurcated portion wherein a distal portion of a bar-shaped operating member is bifurcated, and a projection formed to project in a direction intersecting the longitudinal direction of the operating member.

It is to be noted that in the case where the whole body of the implant, or the implant main body and all the anchor portions, are accommodated in a wrapping bag, the wrapping bag is preferably provided with slits in its portions corresponding to the anchor portions, which can help ensure that a distal portion of the operating member makes direct abutment on the anchor portion by way of the slit, so that the implant can be operated.

In addition, while the case where the puncture apparatus of the present disclosure is applied to an implant for treatment of female urinary incontinence has been described in the above exemplary embodiments, this is not restrictive of the use of the implant.

Examples of the object to which the present disclosure is applicable include pelvic floor diseases inclusive of excretory disorders (urinary urgency, frequent urination, urinary incontinence, fecal incontinence, urinary retention, dysuria, etc.), pelvic organ prolapse, vesicovaginal fistula, urethrovaginal fistula, and pelvic pain, which would be attendant on weakening of the group of pelvic floor muscles. The pelvic organ prolapse include such diseases as cystocele, enterocele, rectocele, and hysterocele, or such diseases as anterior vaginal prolapse, posterior vaginal prolapse, vaginal apical prolapse, and vaginal vault prolapse, which are denominations based on classification of the vaginal wall part being prolapsed.

In addition, examples of overactive tissue include the bladder, vagina, uterus, and bowels. On the other hand, examples of lessactive tissue include bones, muscles, fascias, and ligaments. Especially in relation to the pelvic floor diseases, examples of the lessactive tissue include obturator fascia, coccygeus fascia, cardinal ligament, uterosacral ligament, and sacrospinous ligament.

Examples of the procedure for interlocking an overactive tissue in the pelvic floor disorder with the lessactive tissue, there are included a retropubic sling surgery, a transobturator sling surgery (Transobturator Sling Surgery, Transobturator Tape; TOT), a tension-free vaginal mesh (Tension-free Vaginal Mesh; TVM) surgery, a uterosacral ligament suspension (Uterosacral Ligament Suspension: USLS) surgery, a sacrospinous ligament fixation (Sacrospinous Ligament Fixation: SSLF), an iliococcygeus fascia fixation surgery, and a coccygeus fascia fixation surgery.

The detailed description above describes a method of placing an implant indwelling. The disclosure is not limited, however, to the precise exemplary embodiments and variations described. Various changes, modifications and equivalents can be effected by one skilled in the art without departing from the spirit and scope of the disclosure as defined in the accompanying claims. It is expressly intended that all such changes, modifications and equivalents which fall within the scope of the claims are embraced by the claims.

What is claimed is:

1. A method of placing an implant indwelling in a living body, the method comprising:
forming an insertion hole in the living body, the insertion hole extending from a living body surface and passing a first obturator foramen on a first side of the living body and a second obturator foramen on an opposing second side of the living body, an end portion of the insertion hole on the first side being opened in the living body surface, an end portion of the insertion hole on the opposing second side being closed in relation to the living body surface;
inserting a medical tube into the insertion hole prior to insertion of the implant, the medical tube permitting the implant to be inserted into the medical tube;
inserting the implant into the medical tube inserted in the insertion hole, the implant having an anchor plate on each end of a main body of the implant, wherein each of the anchor plates is divided into a small width portion interlocked to the main body of the implant, a large width portion greater than the small width portion in width, and a decreasing-width portion, and wherein a width of the decreasing-width portion decreases along a direction towards a side opposite to the main body of the implant; and
pulling the medical tube out of the insertion hole so that the implant is placed indwelling in the living body.

2. The method of placing the implant indwelling according to claim 1, comprising:
passing the insertion hole between a urethra and a vagina.

3. The method of placing the implant indwelling according to claim 1, comprising:
forming the insertion hole by a turning operation of a turnable puncture needle having a needle tip by which to puncture the living body, and stopping the turning operation when the needle tip has passed the obturator on the first side and has passed the obturator on the opposing second side.

4. The method of placing the implant indwelling according to claim 1, wherein a length of the implant is shorter than a length of the insertion hole.

5. The method of placing the implant indwelling according to claim 1, comprising:
restricting longitudinal movement of the main body of the implant with the anchor plates in a state where the medical tube has been pulled out and the implant has been thereby placed indwelling in the living body.

6. The method of placing the implant indwelling according to claim 1, comprising:
placing an elongated operating member in abutment on the implant and moving the implant forward in an inserting direction, at the time of inserting the implant into the medical tube.

7. The method of placing the implant indwelling according to claim 6, comprising:
providing the elongated operating member, at an intermediate portion in a longitudinal direction of the operating member, with a marker that indicates a position of the operating member in the living body.

8. A method of placing an implant indwelling in a living body, the method comprising:
forming an insertion hole in the living body, the insertion hole extending from a living body surface and passing a first obturator foramen on a first side of the living body and a second obturator foramen on an opposing second side of the living body, an end portion of the insertion hole on the first side being opened in the living body surface, an end portion of the insertion hole on the opposing second side being closed in relation to the living body surface;
collectively inserting into the insertion hole both a medical tube permitting the implant to be inserted into the medical tube and the implant, the implant having an anchor plate on each end of a main body of the implant, wherein each of the anchor plates is divided into a small width portion interlocked to the main body of the implant, a large width portion greater than the small width portion in width, and a decreasing-width portion, and wherein a width of the decreasing-width portion decreases along a direction towards a side opposite to the main body of the implant, the implant preliminarily inserted in the medical tube; and
pulling the medical tube out of the insertion hole so that the implant is placed indwelling in the living body.

9. The method of placing the implant indwelling according to claim 8, comprising:
passing the insertion hole between a urethra and a vagina.

10. The method of placing the implant indwelling according to claim 8, comprising:
forming the insertion hole by a turning operation of a turnable puncture needle having a needle tip by which to puncture the living body, and stopping the turning operation when the needle tip has passed the obturator on the first side and has passed the obturator on the opposing second side.

11. The method of placing the implant indwelling according to claim 8, wherein a length of the implant is shorter than a length of the insertion hole.

12. The method of placing the implant indwelling according to claim 8, comprising:
restricting longitudinal movement of a main body of the implant with the anchor plates in a state where the medical tube has been pulled out and the implant has been thereby placed indwelling in the living body.

13. The method of placing the implant indwelling according to claim 8, comprising:
placing an elongated operating member in abutment on the implant and moving the implant forward in an inserting direction, at the time of inserting the implant into the medical tube.

14. The method of placing the implant indwelling according to claim 13, comprising:
providing the elongated operating member, at an intermediate portion in a longitudinal direction of the operating member, with a marker that indicates a position of the operating member in the living body.

* * * * *